US007700092B2

(12) United States Patent
Conzelmann

(10) Patent No.: US 7,700,092 B2
(45) Date of Patent: Apr. 20, 2010

(54) PNEUMOVIRUS NS PROTEINS ANTAGONIZE THE INTERFERON IFN RESPONSE

(75) Inventor: Karl-Klaus Conzelmann, Neuried (DE)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/880,914

(22) Filed: Jul. 24, 2007

(65) Prior Publication Data

US 2008/0160039 A1 Jul. 3, 2008

Related U.S. Application Data

(63) Continuation of application No. 10/258,825, filed as application No. PCT/EP01/04740 on Apr. 26, 2001, now abandoned.

(30) Foreign Application Priority Data

Apr. 26, 2000 (DE) ................................. 100 20 505

(51) Int. Cl.
*A61K 48/00* (2006.01)
(52) U.S. Cl. .................................................. 424/93.2
(58) Field of Classification Search .................. 424/93.2
See application file for complete search history.

(56) References Cited

U.S. PATENT DOCUMENTS

| 6,699,476 B1 | 3/2004 | Collins et al. | |
|---|---|---|---|
| 6,844,188 B1 * | 1/2005 | MacDonald et al. | 435/320.1 |
| 6,923,971 B2 * | 8/2005 | Krempl et al. | 424/211.1 |
| 2003/0083305 A1 * | 5/2003 | Palese et al. | 514/44 |

FOREIGN PATENT DOCUMENTS

| WO | WO 97/17090 | * | 5/1997 |
|---|---|---|---|
| WO | WO 98 02530 | | 1/1998 |
| WO | WO 99 64068 | | 12/1999 |

OTHER PUBLICATIONS

Tolley et al. Vaccine 14:1637-1646, 1996.*
Ahmadian G. et al., J Gen Virol 80 (Pt 8) 2011-2016 (1999).
Atreya, P.L. and Kulkarni, S., Virology 261:227-241 (1999).
Atreya, P.L. et al., J. Virol 72:1452-1461 (1998).
Bermingham, A. and Collins, P.L., Proc Natl Acad Sci USA 96:11259-11264 (1999).
Buchholz, U.J. et al., J Virol 73:251-259 (1999).
Buchholz, U.J. et al., J. Virol 74:1187-1199 (2000).
Chaplin, P.J. et al., Immunogenetics 44: 143-145 (1996).
Collins, P.L. et al., Proc Natl Acad Sci USA 92:11563-11567 (1995).
Collins, P.L. et al., pp. 1313-1351 of vol. 1, Fields Virology, B.N. Fields et al Eds., (3rd ed. Raven Press, 1996).
Collins, P.L. and Wertz, G.W., Virology 143:442-451 (1985).
Conzelmann, K.K., Annu Rev Genet 32:123-162 (1998).
Conzelmann, K.K. et al., Virology 175:485-499 (1990).
Didcock, L. et al., J Virol 73:3125-3133 (1999).
Finke, S. and Conzelmann, K.K., J Virol 71:7281-7288 (1997).
Finke, S. and Conzelman, K.K., J Virol 73:3818-3825 (1999).
Gale, M.J. et al., Mol Cell Biol 18:5208-5218 (1998).
Gale, M.J. et al., Virology 230:217-227 (1997).
Garcin, D. et al., J Virol 73:6559-6565 (1999).
Garcia-Sastre, A. et al., J Virol 72:8550-8558 (1998).
Garcia-Sastre, A. et al., Virology 252:324-330 (1998).
Grosfeld, H. et al., J Virol 69:5677-5686 (1995).
Hanada, N. et al., J Med Virol 20:363-370 (1986).
Hardy, R.W. and Wertz, G.W., J Virol 72:520-526 (1998).
Jin, H. et al., J Virol 74:74-82 (2000).
Jin, H. et al., Virology 251:206-214 (1998).
Lerch, R.A. et al., J Virol 63:833-840 (1989).
Mallipeddi, S.K. et al., Arch Virol 115:23-36 (1990).
Mebatsion, T. et al., Proc Natl Acad Sci USA 93:7310-7314 (1996).
Mohanty, S.B. et al., Am J Vet Res 36:417-419 (1975).
Pastey, M.K. and Samal, S.K., J Gen Virol 76:193-197 (1995).
Ploegh, H.L., Science 280:248-253 (1998).
Pringle, C.R., Arch Virol 141:2251-2256 (1996).
Pringle, C.R., Arch Virol 143:203-210 (1998).
Samal, S.K. et al., Virology 193:470-473 (1993).
Schlender J. et al., J. Virol 74:8234-8242 (2000).
Schnell, M.J. et al., EMBO J 13:4195-4203 (1994).
Stott, E.J. et al., J Hyg (Lond)93:251-261 (1984).
Tan, S.L. and Katze, M.G., J Interferon Cytokine Res 18:757-766 (1998).
Taylor, D.R. et al., Science 285:107-110 (1999).
Teng, M.N. and Collins, P.L., J Virol 73:466-473 (1999).
Uzé, G. et al., J Interferon Cytokine Res 15:3-26 (1995).
Van der Poel, W.H. et al., J Infect 29:215-228 (1994).
Wathelet, M.G. et al., Eur J Biochem 206:901-910 (1992).
Weber, E., et al., Respiration 62:27-33 (1995).
Whitehead, S.S. et al., J Virol 73:3438-3442 (1999).
Yu, Q. et al., J Virol 69:2412-2419 (1995).
Didcock, L. et al., J Virol 73:9928-9933 (1999).
Evans, J.E. et al., Virus Research 43:155-161 (1996).

* cited by examiner

Primary Examiner—Brian Whiteman
(74) Attorney, Agent, or Firm—Maria Restrepo-Hartwig; J. Darrell Fontenot

(57) ABSTRACT

The present invention relates to the use of a pneumovirus NS1 protein and/or NS2 protein or a nucleic acid encoding pneumovirus NS1 protein and/or NS2 protein for the preparation of a pharmaceutical formulation for reducing the immune response mediated by interferon (IFN). The invention further relates to recombinant pneumoviruses, in particular respiratory syncytial viruses (RSV), having an increased, reduced, or lacking a resistance to the interferon (IFN) mediated immune response, recombinant viruses having an increased resistance to the interferon (IFN) mediated immune response, and the use of the viruses in pharmaceutical applications, e.g. as vaccines.

15 Claims, 19 Drawing Sheets

Virus- or Mock-infected Effector Cells ( EC )

infectious Virus ✗ soluble Factors ↓

NS-Deletion Mutants or BRSV-infected Responder Cells (RC)

FIG. 4A

| rBRSV | Survival of MDBK Cells | | Survival of bovine Macrophages | |
|---|---|---|---|---|
| | % inhibition | -fold reduction | % inhibition | -fold reduction |
| Δ NS1 | 37 +/- 21 | 1.6 | 92 +/- 6 | 31 |
| Δ NS2 | 61 +/- 15 | 2.6 | 96 +/- 3 | 40 |
| Δ NS1/2 | 86 +/- 7 | 6.7 | 99 +/- 1 | 53 |
| wt | 6 +/- 5 | 1.05 | 12 +/- 7 | 1.3 |

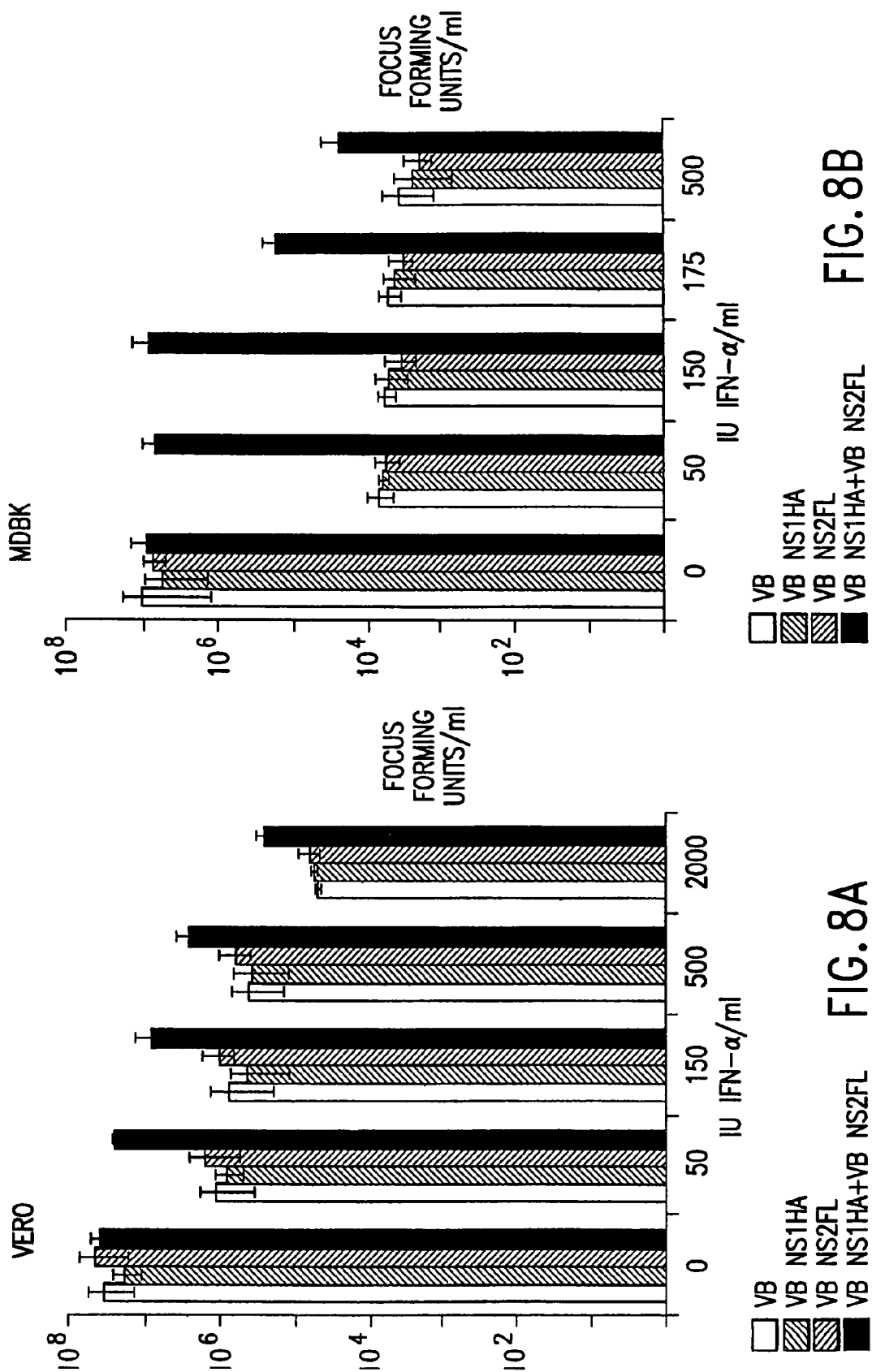

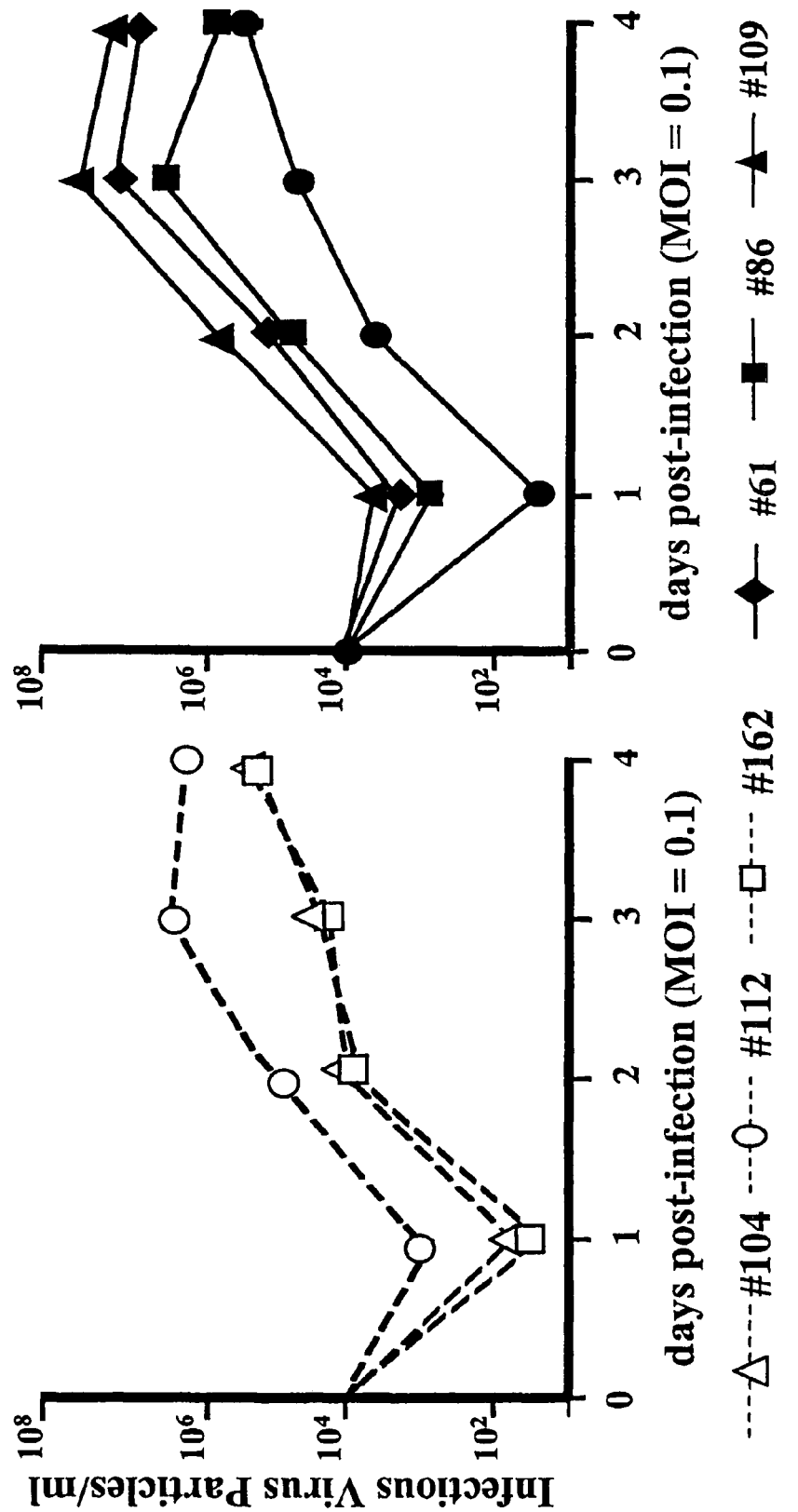

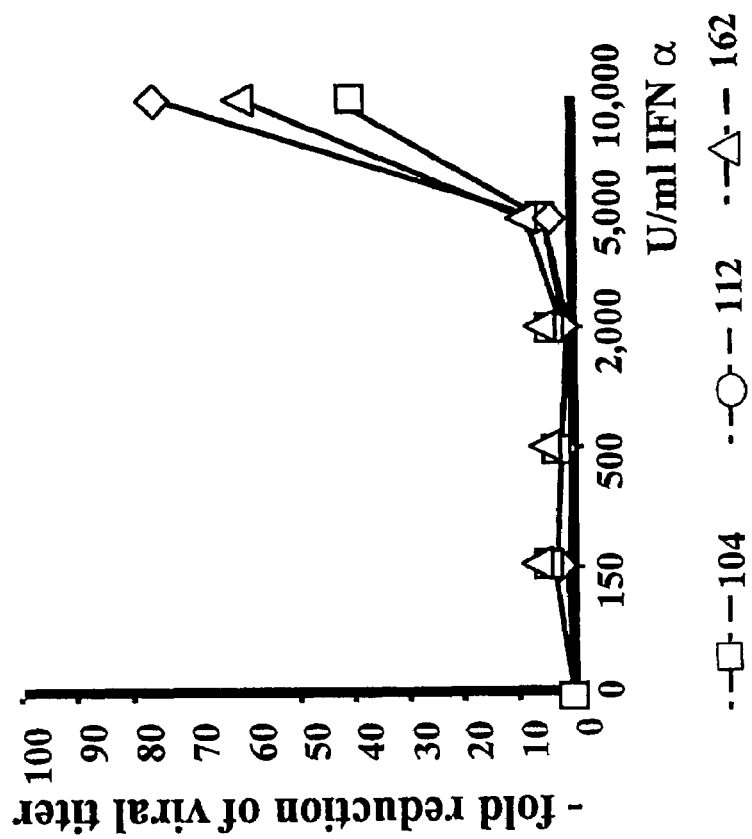
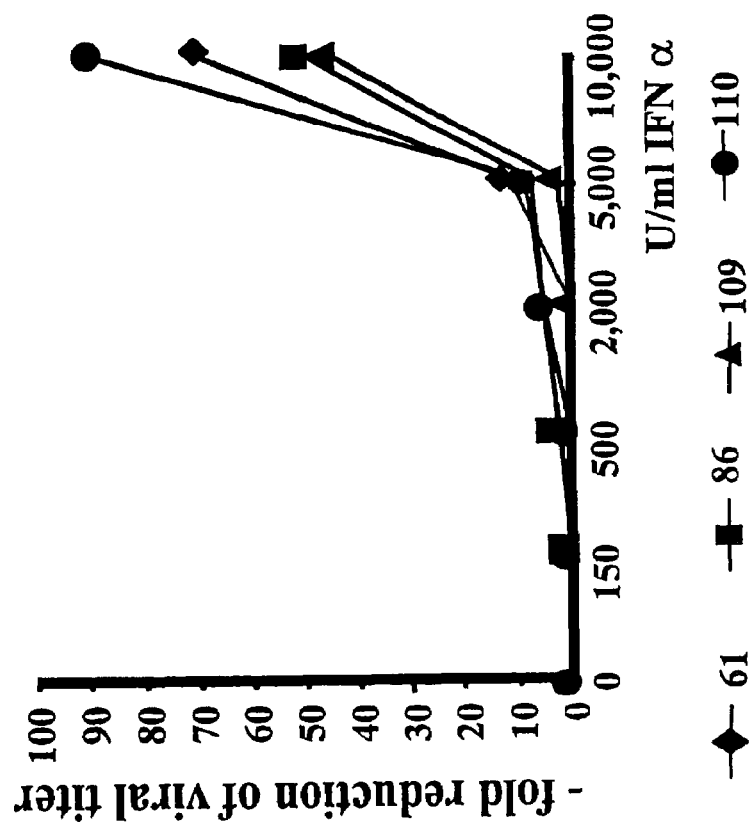

FIG. 15

| | | | |
|---|---|---|---|
| (SEQ ID NO:17) | hNS1 | MGSNSLSMIKVRLQNLFDNDEVALLKITCYTDKLIHLTNA | 40 |
| (SEQ ID NO:18) | bNS1 | MGSETLSVIQVRLRNIYDNDKVALLKITCHTNRLILLTHT | 40 |
| (SEQ ID NO:19) | mNS1 | MGCN......VMMELDYGGRAAWLAFHITNFDRSDLETIL | 34 |
| | hNS1 | LAKAVIHTIKLNGIVFVHVITSSDICPNNNIVVKSNFTTM | 80 |
| | bNS1 | LAKSVIHTIKLSGIVFIHIITSSDVCPTSDIINSANFTSM | 80 |
| | mNS1 | RGARVCNTWQDQ..RLSVYLVGRDCNLLRPFVQAAKFIHN | 72 |
| | hNS1 | PVLQNGGYIWEMMELTHCSQPNGLIDDNCEIKFSKKLSDS | 120 |
| | bNS1 | PILQNGGYIWELMELTHCFQTNGLIDDNCEITFSKRLSDS | 120 |
| | mNS1 | TRR..G......QTLTIWFTKN.......IVFSSTG..Q | 94 |
| | hNS1 | TMTNYMNQLSELLGFDLNP | 139 |
| | bNS1 | ELAKYSNQLSTLLGLN | 136 |
| | mNS1 | ETEPPIDPTCELLVELISG | 113 |

FIG.18A

| | | | |
|---|---|---|---|
| (SEQ ID NO:20) | hNS2 | MDTTHNDNTPQR......LMITDMR.......... | 19 |
| (SEQ ID NO:21) | bNS2 | MSTPNPETTAQR......LIVNDMR.......... | 19 |
| (SEQ ID NO:22) | mNS2 | MSIAMNKFTQTISKPATILNISDSEESGDEAGVGKVSRTT | 40 |
| | hNS2 | ......PLSLETITSLT..RDIITHRFIYLINHECIVR | 50 |
| | bNS2 | ......PLSIETIISLT..KDITHTFIYLINHECIVR | 50 |
| | mNS2 | QSSERWLDLLIEKFQPSLQNITRYINWNFIRICNDRLKKE | 80 |
| | hNS2 | KLDERQATFTFLVNYEKKLLHKVGSTKYKKYT..EYNTKY | 88 |
| | bNS2 | KLDERQATFTFLVNYEKKLLHKVGSTKYNKYT..EYNRKY | 88 |
| | mNS2 | KMGYIEAKQYVEDMAWNVIASEADSIEWKCIRRQEKVTGV | 120 |
| | hNS2 | GTFPMPIFINHDGFLECIGIKPTKHTPIIYKYDLNP | 124 |
| | bNS2 | GTFPMPIFINHDGFLECIGIKPTRNTPIIYKYDLNP | 124 |
| | mNS2 | KYPKFFFVQHKEDWIECTGCIPYPGHDLIYDEDDDD | 156 |

FIG.18B

SEQUENCE LISTING

```
<160> NUMBER OF SEQ ID NOS: 22

<210> SEQ ID NO 1
<211> LENGTH: 33
<212> TYPE: DNA
<213> ORGANISM: Artificial
<220> FEATURE:
<223> OTHER INFORMATION: Primer NNot (+)

<400> SEQUENCE: 1
taggcggccg caaaaatggc tcttaggaag gtg                                    33

<210> SEQ ID NO 2
```

```
<211> LENGTH: 21
<212> TYPE: DNA
<213> ORGANISM: Artificial
<220> FEATURE:
<223> OTHER INFORMATION: Primer Nstu (-)

<400> SEQUENCE: 2
tcctttgtat cgtttcattt c                                        21

<210> SEQ ID NO 3
<211> LENGTH: 60
<212> TYPE: DNA
<213> ORGANISM: Artificial
<220> FEATURE:
<223> OTHER INFORMATION: Primer NS1HAr-EcoRI

<400> SEQUENCE: 3
gcaatagaat tcctaagcgt aatctggtac atcataagga taattcagac caagaagagt    60

<210> SEQ ID NO 4
<211> LENGTH: 60
<212> TYPE: DNA
<213> ORGANISM: Artificial
<220> FEATURE:
<223> OTHER INFORMATION: Primer NS2FLr-EcoRI

<400> SEQUENCE: 4
gcaatagaat tcctatttat cgtcatcatc tttataatct ggatttaaat catacttata    60

<210> SEQ ID NO 5
<211> LENGTH: 24
<212> TYPE: DNA
<213> ORGANISM: Artificial
<220> FEATURE:
<223> OTHER INFORMATION: Primer hNS1-NcoI5

<400> SEQUENCE: 5
attgaccatg ggcagcaatt catt                                     24

<210> SEQ ID NO 6
<211> LENGTH: 29
<212> TYPE: DNA
<213> ORGANISM: Artificial
<220> FEATURE:
<223> OTHER INFORMATION: Primer hNS1-EcoRI5

<400> SEQUENCE: 6
attgagaatt cttatggatt aagatcaaa                                29

<210> SEQ ID NO 7
<211> LENGTH: 23
<212> TYPE: DNA
<213> ORGANISM: Artificial
<220> FEATURE:
<223> OTHER INFORMATION: Primer hNS2-NcoI5

<400> SEQUENCE: 7
attgaccatg gacacaaccc aca                                      23

<210> SEQ ID NO 8
<211> LENGTH: 29
<212> TYPE: DNA
<213> ORGANISM: Artificial
<220> FEATURE:
<223> OTHER INFORMATION: Primer hNS1-NotI5

<400> SEQUENCE: 8
```
attgagaatt cttatggatt gagatcata                               29

<210> SEQ ID NO 9
<211> LENGTH: 57
<212> TYPE: DNA
<213> ORGANISM: Artificial
<220> FEATURE:
<223> OTHER INFORMATION: Primer hNS1-NotI5

<400> SEQUENCE: 9
tatgaagcgg ccgcccctc tcttctttct acagaaaatg gcagcaatt cattgag     57

<210> SEQ ID NO 10
<211> LENGTH: 62
<212> TYPE: DNA
<213> ORGANISM: Artificial
<220> FEATURE:
<223> OTHER INFORMATION: Primer hNS2-AseI5

<400> SEQUENCE: 10
atacttatta attggggcaa ataaatcagt tccccaacca gccatggaca caacccacaa   60
tg                                                                  62

<210> SEQ ID NO 11
<211> LENGTH: 72
<212> TYPE: DNA
<213> ORGANISM: Artificial
<220> FEATURE:
<223> OTHER INFORMATION: Primer hNS2-Acc65I3

<400> SEQUENCE: 11
ataaatggta ccaaaagata acactgtgtg aattaaattt tgaaaagtgc ttatggattg   60
agatcatact tg                                                       72

<210> SEQ ID NO 12
<211> LENGTH: 60
<212> TYPE: DNA
<213> ORGANISM: Artificial
<220> FEATURE:
<223> OTHER INFORMATION: Primer mNS1-NotIEcoRV5

<400> SEQUENCE: 12
aatgatatcg cggccgcccc ctctcttctt tctacagaaa tgggctgtaa tgtgatgatg   60

<210> SEQ ID NO 13
<211> LENGTH: 62
<212> TYPE: DNA
<213> ORGANISM: Artificial
<220> FEATURE:
<223> OTHER INFORMATION: Primer mNS1ha-EcoRI/V3

<400> SEQUENCE: 13
aatgatatcg aattcttaag cgtaatcggt acatcataag gataaccact gatcagctct   60
ac                                                                  62

<210> SEQ ID NO 14
<211> LENGTH: 67
<212> TYPE: DNA
<213> ORGANISM: Artificial
<220> FEATURE:
<223> OTHER INFORMATION: Primer mNS2-AseIEcoRV5

<400> SEQUENCE: 14

```
aatgatatca ttaattgggg caaataaatc agttcccccaa ccagccatgt ccacagctat    60
gaacaag                                                              67
```

<210> SEQ ID NO 15
<211> LENGTH: 57
<212> TYPE: DNA
<213> ORGANISM: Artificial
<220> FEATURE:
<223> OTHER INFORMATION: Primer mNS2f1-EcoRI/V3

<400> SEQUENCE: 15

```
aatgatatcg aattctcatt tatcgtcatc atctttatag tcatcatcat cctcatc       57
```

<210> SEQ ID NO 16
<211> LENGTH: 75
<212> TYPE: DNA
<213> ORGANISM: Artificial
<220> FEATURE:
<223> OTHER INFORMATION: Primer mNS2-Acc65I3

<400> SEQUENCE: 16

```
ataaatggta ccaaaagata acactgtgtg aattaaattt tgaaaagtgc tcatttatcg    60
tcatcatctt tatag                                                     75
```

<210> SEQ ID NO 17
<211> LENGTH: 139
<212> TYPE: PRT
<213> ORGANISM: Human respiratory syncytial virus NS1

<400> SEQUENCE: 17

```
Met Gly Ser Asn Ser Leu Ser Met Ile Lys Val Arg Leu Gln Asn Leu
1               5                   10                  15

Phe Asp Asn Asp Glu Val Ala Leu Leu Lys Ile Thr Cys Tyr Thr Asp
                20                  25                  30

Lys Leu Ile His Leu Thr Asn Ala Leu Ala Lys Ala Val Ile His Thr
            35                  40                  45

Ile Lys Leu Asn Gly Ile Val Phe Val His Val Ile Thr Ser Ser Asp
        50                  55                  60

Ile Cys Pro Asn Asn Asn Ile Val Val Lys Ser Asn Phe Thr Thr Met
65                  70                  75                  80

Pro Val Leu Gln Asn Gly Gly Tyr Ile Trp Glu Met Met Glu Leu Thr
                85                  90                  95

His Cys Ser Gln Pro Asn Gly Leu Ile Asp Asp Asn Cys Glu Ile Lys
            100                 105                 110

Phe Ser Lys Lys Leu Ser Asp Ser Thr Met Thr Asn Tyr Met Asn Gln
        115                 120                 125

Leu Ser Glu Leu Leu Gly Phe Asp Leu Asn Pro
    130                 135
```

<210> SEQ ID NO 18
<211> LENGTH: 136
<212> TYPE: PRT
<213> ORGANISM: Bovine respiratory syncytial virus

<400> SEQUENCE: 18

```
Met Gly Ser Glu Thr Leu Ser Val Ile Gln Val Arg Leu Arg Asn Ile
1               5                   10                  15

Tyr Asp Asn Asp Lys Val Ala Leu Leu Lys Ile Thr Cys His Thr Asn
                20                  25                  30
```

Arg Leu Ile Leu Leu Thr His Thr Leu Ala Lys Ser Val Ile His Thr
            35                  40                  45

Ile Lys Leu Ser Gly Ile Val Phe Ile His Ile Ile Thr Ser Ser Asp
 50                  55                  60

Tyr Cys Pro Thr Ser Asp Ile Ile Asn Ser Ala Asn Phe Thr Ser Met
 65                  70                  75                  80

Pro Ile Leu Gln Asn Gly Gly Tyr Ile Trp Glu Leu Met Glu Leu Thr
                 85                  90                  95

His Cys Phe Gln Thr Asn Gly Leu Ile Asp Asp Asn Cys Glu Ile Thr
            100                 105                 110

Phe Ser Lys Arg Leu Ser Asp Ser Glu Leu Ala Lys Tyr Ser Asn Gln
            115                 120                 125

Leu Ser Thr Leu Leu Gly Leu Asn
            130                 135

<210> SEQ ID NO 19
<211> LENGTH: 113
<212> TYPE: PRT
<213> ORGANISM: Mouse respiratory syncytial virus NS1

<400> SEQUENCE: 19

Met Gly Cys Asn Val Met Met Glu Leu Asp Tyr Gly Gly Arg Ala Ala
 1               5                  10                  15

Trp Leu Ala Phe His Ile Thr Asn Phe Asp Arg Ser Asp Leu Glu Thr
                 20                  25                  30

Ile Leu Arg Gly Ala Arg Val Cys Asn Thr Trp Gln Asp Gln Arg Leu
            35                  40                  45

Ser Val Tyr Leu Val Gly Arg Asp Cys Asn Leu Leu Arg Pro Phe Val
 50                  55                  60

Gln Ala Ala Lys Phe Ile His Asn Thr Arg Arg Gly Gln Thr Leu Thr
 65                  70                  75                  80

His Trp Phe Thr Lys Asn Ile Val Phe Ser Ser Thr Gly Gln Glu Thr
                 85                  90                  95

Glu Pro Pro Ile Asp Pro Thr Cys Glu Leu Leu Val Gly Leu Ile Ser
            100                 105                 110

Gly

<210> SEQ ID NO 20
<211> LENGTH: 124
<212> TYPE: PRT
<213> ORGANISM: Human respiratory syncytial virus NS2

<400> SEQUENCE: 20

Met Asp Thr Thr His Asn Asp Asn Thr Pro Gln Arg Leu Met Ile Thr
 1               5                  10                  15

Asp Met Arg Pro Leu Ser Leu Glu Thr Thr Ile Thr Ser Leu Thr Arg
                 20                  25                  30

Asp Ile Ile Thr His Arg Phe Ile Tyr Leu Ile Asn His Glu Cys Ile
            35                  40                  45

Val Arg Lys Leu Asp Glu Arg Gln Ala Thr Phe Thr Phe Leu Val Asn
 50                  55                  60

Tyr Glu Met Lys Leu Leu His Lys Val Gly Ser Thr Lys Tyr Lys Lys
 65                  70                  75                  80

Tyr Thr Glu Tyr Asn Thr Lys Tyr Gly Thr Phe Pro Met Pro Ile Phe
                 85                  90                  95

Ile Asn His Asp Gly Phe Leu Glu Cys Ile Gly Ile Lys Pro Thr Lys

```
                    100                 105                 110

His Thr Pro Ile Ile Tyr Lys Tyr Asp Leu Asn Pro
        115                 120

<210> SEQ ID NO 21
<211> LENGTH: 124
<212> TYPE: PRT
<213> ORGANISM: Bovine respiratory syncytial virus NS2

<400> SEQUENCE: 21

Met Ser Thr Pro Asn Pro Glu Thr Thr Ala Gln Arg Leu Ile Val Asn
1               5                   10                  15

Asp Met Arg Pro Leu Ser Ile Glu Thr Glu Ile Ile Ser Leu Thr Lys
            20                  25                  30

Asp Ile Ile Thr His Thr Phe Ile Tyr Leu Ile Asn His Glu Cys Ile
        35                  40                  45

Val Arg Lys Leu Asp Glu Arg Gln Ala Thr Phe Thr Phe Leu Val Asn
    50                  55                  60

Tyr Glu Met Lys Leu Leu His Lys Val Gly Ser Thr Lys Tyr Asn Lys
65                  70                  75                  80

Tyr Thr Glu Tyr Asn Arg Lys Tyr Gly Thr Phe Pro Met Pro Ile Phe
                85                  90                  95

Ile Asn His Asp Gly Phe Leu Glu Cys Ile Gly Ile Lys Pro Thr Arg
            100                 105                 110

Asn Thr Pro Ile Ile Tyr Lys Tyr Asp Leu Asn Pro
        115                 120

<210> SEQ ID NO 22
<211> LENGTH: 156
<212> TYPE: PRT
<213> ORGANISM: Mouse respiratory syncytial virus NS2

<400> SEQUENCE: 22

Met Ser Thr Ala Met Asn Lys Phe Thr Gln Thr Ile Ser Lys Pro Ala
1               5                   10                  15

Thr Ile Leu Asn Ile Ser Asp Ser Glu Glu Ser Gly Asp Glu Ala Gly
            20                  25                  30

Val Gly Lys Val Ser Arg Thr Thr Gln Ser Ser Glu Arg Trp Leu Asp
        35                  40                  45

Leu Leu Ile Glu Lys Phe Gln Pro Ser Leu Gln Asn Ile Thr Arg Tyr
    50                  55                  60

Ile Asn Trp Asn Phe Ile Arg Ile Cys Asn Asp Arg Leu Lys Lys Glu
65                  70                  75                  80

Lys Met Gly Tyr Ile Glu Ala Lys Gln Tyr Val Glu Asp Met Ala Trp
                85                  90                  95

Met Val Ile Ala Ser Glu Ala Asp Ser Ile Glu Trp Lys Cys Ile Arg
            100                 105                 110

Arg Gln Glu Lys Val Thr Gly Val Lys Tyr Pro Lys Phe Phe Phe Val
        115                 120                 125

Gln His Lys Glu Asp Trp Ile Glu Cys Thr Gly Cys Ile Pro Tyr Pro
    130                 135                 140

Gly His Asp Leu Ile Tyr Asp Glu Asp Asp Asp
145                 150                 155
```

PNEUMOVIRUS NS PROTEINS ANTAGONIZE THE INTERFERON IFN RESPONSE

This Application is a continuation of U.S. application Ser. No. 10/258,825, filed Oct. 25, 2002, now abandoned, which is a U.S. National Entry of PCT/EP01/04740, filed Apr. 26, 2001, which claims priority to German Provisional Application No. 100 20 505.4, filed Apr. 26, 2000.

BACKGROUND OF THE INVENTION

The present invention relates to the use of a pneumovirus NS1 protein and/or NS2 protein or a nucleic acid encoding pneumovirus NS1 protein and/or NS2 protein for the preparation of a pharmaceutical formulation for reducing the immune response mediated by interferon (IFN). The invention further relates to recombinant pneumoviruses, in particular respiratory syncytial viruses (RSV), having an increased, reduced, or lacking a resistance to the interferon (IFN) mediated immune response of the host, recombinant viruses having an increased resistance to the interferon (IFN) mediated immune response, and the use of these viruses in pharmaceutical formulations, e.g. as vaccines.

DESCRIPTION OF THE PRIOR ART

The bovine respiratory syncytial virus (BRSV) is the most important etiological agent of diseases of the respiratory tract in calves and causes important economical losses (40; 45). The immune response and the pathology in calves mimics symptoms caused by the human respiratory syncytial virus (HRSV) which still is the predominant cause of serious bronchiolitis and pneumonia in infants and young children worldwide (9). Molecular cloning of HRSV and BRSV as well of a related virus, pneumonia virus of mice (PVM) has not only confirmed a close relationship between BRSV and HRSV but has also revealed that they share essential differences with respect to other members of the family Paramyxoviridae leading to the establishment of the subfamily of Pneumovirinae within the Paramyxoviridae family (36; 37). Within this subfamily, the RSV viruses and PVM form the genus *Pneumovirus* while the avian pneumovirus (APV) up to now is the only member of the genus *Metapneumovirus*.

As with all members of the order Mononegavirales the about 15 kb genomic RNA of RSV and PVM is contained in a ribonucleoprotein (RNP) complex acting as template for the sequential transcription of genes (25; 49). Eleven proteins are expressed by 10 transcriptional units arranged in the order 3'-NS1-NS2-N-P-M-SH-G-F-M2-L-5' (5; 9; 30;31). The proteins encoded comprise five RNP associated proteins: the nucleoprotein (N), the phosphoprotein (P), the large catalytic subunit of RNA polymerase (L), and a transcription elongation factor (M2-1) encoded by the first of two overlapping open reading frames of the M2 gene (8; 17; 27; 38). The second open reading frame of the M2 transcriptional unit (M2-2) encodes a non-essential protein as described (1) presumably involved in the regulation of RNA synthesis (4; 28). Three viral proteins are associated with the virus envelope: the fusion protein F, the supposed attachment protein G, and a small hydrophobic protein SH.

The presence of two non-structural protein genes in a 3'-terminal position of the genome distinguishes the members of the genus *Pneumovirus* from all other members of the order Mononegavirales. Due to their position close to the 3'-terminus the NS genes are transcribed in excess. The proteins encoded were detected in infected cells (10; 16). The BRSV NS genes encode polypeptides with 136 and 124 amino acids. A comparison to NS proteins of HRSV from subgroups A and B showed amino acid homologies of 69% and 68% for the NS1 proteins and of 84% and 83% for the NS2 proteins (5; 34). The PVM NS1 and NS2 proteins show no significant homology to the RSV NS genes (about 20% identity) but nevertheless have an analogous function. The derived sequences, however, revealed no obvious indication as to the function of NS proteins in the life cycle of the virus. It has been reported that the HRSV NS1 protein is associated with the M protein while the NS2 protein showed no detectable association with RSV structural proteins indicating different functions for NS1 and NS2 (16; 47). Recently, an inhibitory function of NS1 on the transcription of viral RNA has been suggested by experiments in which artificial HRSV minigenomes were grown in the absence and presence of NS1. In addition, in the same study an inhibitory effect was also observed for NS2 but this effect for NS2 was much less pronounced (3).

Recently established methods for the preparation ("recovery") of infectious negative strand RNA viruses from cDNA (11) have enabled the generation of recombinant human (8; 29) and bovine (5) RSV and the examination of individual protein functions in the viral context. The successful preparation of viable NS2 gene deletion mutants confirmed that NS2 is not essential for virus replication in cell culture (5; 43). The pattern and the relative amounts of mRNAs and full length RNA produced in infected cells were not visibly altered. The deletion mutants, however, were attenuated, showed slower growth rates and provided lower infectious virus titers compared to the starting virus. Thus, although NS2 is non-essential it represents an accessory factor which is capable of substantially supporting virus growth by a so far unknown mechanism. Up to now, however, the function of the NS protein remains unknown.

SUMMARY OF THE INVENTION

This invention is based on the discovery that the NS1 and/or NS2 proteins of RSV and RSV-related viruses, particularly those of the genus *Pneumovirus* (RSV and PVM) all of which will be referred to as "RSV" in the following have an antagonistic effect on the IFN mediated immune response.

The present invention relates to the use of an RSV NS1 and/or NS2 protein or of a nucleic acid sequence encoding RSV NS1 or of a nucleic acid sequence encoding RSV NS2 for the preparation of a pharmaceutical formulation for the reduction on the immune response mediated by IFN, preferably by IFN alpha and/or beta.

Another aspect of the present invention relates to a method for the reduction of the IFN mediated immune response in an animal comprising the administration of RSV NS1 and/or NS2 protein or a nucleic acid encoding RSV NS1 protein or a nucleic acid encoding NS2 protein. Particularly, the invention relates to the use of the RSV NS1 and/or NS2 proteins or the nucleic acids encoding these proteins for the modification of the IFN mediated immune response by inhibiting the IFN mediated antiviral response.

In a preferred embodiment of the present invention the RSV NS1 protein is used in combination with the NS2 protein for the preparation of a pharmaceutical formulation, or a nucleic acid sequence encoding RSV NS1 protein is used in combination with a nucleic acid sequence encoding RSV NS2 protein for the preparation of a pharmaceutical formulation to reduce the IFN mediated immune response. "In combination" according to the present invention relates to either a simultaneous or successive administration.

In another aspect of the present invention the RSV NS1 and/or NS2 proteins are used to protect a non-related virus from the IFN mediated immune response. Preferably, the RSV NS1 and/or NS2 proteins are the BRSV NS proteins. The NS1 and NS2 proteins protect a non-related virus in a cooperative manner. "Non-related virus" according to the present invention refers to viruses which do not express the RSV NS1 and/or NS2 protein. In a preferred embodiment the virus is the rabies virus. Preferably, the RSV NS1 and/or NS2 proteins are expressed from the viral nucleic acid.

In another aspect the pharmaceutical formulation of the invention containing the RSV NS1 and/or NS2 protein or a nucleic acid sequence encoding RSV NS1 and/or a nucleic acid sequence encoding NS2 and which reduces the IFN mediated immune response further comprises a vaccine. Preferably, an administration of the vaccine together with the pharmaceutical formulation results in a reduced elimination of the vaccine from the body to which it is administered.

The invention also relates to the application of altered RSV NS1 and/or NS2 proteins for the preparation of a pharmaceutical formulation for modulation of the IFN mediated immune response. In a preferred embodiment the alteration results in an enhanced IFN modulating activity of the NS1 and/or NS2 protein.

The present invention relates to the use of a recombinant RSV carrying a modified nucleic acid sequence encoding NS1 and/or NS2 for the preparation of a vaccine wherein the modification decreases or abolishes the capability of the virus to escape an IFN mediated immune response. In a preferred embodiment the modified nucleic acid sequences encoding NS1 and/or NS2 are homologous or heterologous to said recombinant RSV. Particularly preferred are applications wherein the recombinant RSV is derived from human, bovine RSV or from PVM.

In addition, the present invention comprises RSVs having an altered host range wherein the nucleic acid sequence encoding NS1 and/or NS2 of RSV is replaced by a nucleic acid sequence encoding NS1 and/or NS2 from a different RSV which is capable of infecting the desired host, as well as methods for the generation of such RSVs having an altered host cell tropism.

DETAILED DESCRIPTION OF THE INVENTION

To study the function of the RSV proteins in more detail BRSV deletion mutants lacking the NS1 gene or the NS1 and NS2 genes were generated and studied for their behavior in different cell lines.

A first indication as to an increased sensitivity of the NS deletion mutants with respect to host cell factors was observed after infection of MDBK cells which are fully sensitive for a wt BRSV infection and provide higher wt BRSV titers than all other cell lines tested. Viruses lacking one or both NS genes, however, grew worst in MDBK cells while in other cell lines such as Vero or BSR an absence of the NS genes resulted in only a 10 fold reduction in infectious titers. Co-cultivation experiments identified type I interferons as the crucial host cell factors produced by BRSV infected MDBK cells. Obviously, an antiviral status is induced in infected MDBK cultures by autocrine and paracrine cells stimulation. Although wt BRSV is able to counteract this response none of the NS deletion mutants shares this capability. Vero cells on the other hand lack the type I interferon genes (15; 46) so that the virus infection does not result in induction of an antiviral status and enable growth of the NS deletion mutants. Although Vero cells are not capable of interferon production they can react to a stimulation by exogenous interferon by means of JAK/STAT mediated signaling via the IFN alpha receptor (IFNAR) complex. Bovine interferons secreted by the infected MDBK cells induced an antiviral response in Vero "responder" cells suppressing the growth of the NS deletion mutants but not of wt BRSV. The antiviral effect caused by MDBK supernatants was prevented by incubation of Vero cells with an antibody blocking IFN binding to IFNAR. Thus, the only active components of MDBK cell supernatants in induction of the antiviral response were IFN alpha and/or IFN beta.

With a reduction of the double deletion mutant of maximal 7 fold the inhibitory effect on the NS deletion mutants in Vero cells treated with MDBK cell supernatants was weak and thus not comparable to the severe inhibition of the NS deletion mutants in MDBK cells. This may be attributed to several factors. Presumably, the stimulation of the primate derived Vero cells with heterologous IFN of bovine origin is less efficient compared to the stimulation of MDBK. Similar to the situation in man different types of bovine IFN alpha (types 2 to 8) and IFN beta (types 1 and 3) were identified showing different biological activities (7). Furthermore, the antiviral mechanisms of Vero cells appear to be less efficient than those of MDBK. Supernatants of activated and infected macrophages known to secrete higher amounts of type I interferon than other cells caused an enhanced up to 50 fold reduction of the NS deletion mutants in Vero "responder" cells. By stimulating Vero cells with recombinant human IFN alpha A/D or IFN beta, the replication of the NS deletion mutants could be inhibited in a dose-dependent manner wherein 500 units almost completely inhibited the replicative activity.

Therefore, by the present invention RSV proteins have been identified as antagonists of the IFN mediated host cell response.

Moreover, using another negative strand RNA virus, the rabies virus, as a vector for the expression of the BRSV derived NS gene the activity of the two NS proteins NS1 and NS2 was shown to be able to increase the IFN resistance of a non-related virus. Another finding was that the NS1 and NS2 proteins may be derived from different RSVs.

In summary, an important biological function could be attributed to the RSV NS proteins in that they mediate a protection of the virus against cellular interferon mediated antiviral mechanisms (IFN antagonizing effect). Moreover, it was unexpectedly found that by using both NS proteins in combination said IFN antagonizing effect is multiplied. This is the first example of a cooperation of two viral proteins in the antagonism to interferon.

The adaptation of viral proteins to counteract innate immune responses within cells of their natural host is supposed to be an important factor for determining the viral host range and may prevent viruses from crossing species barriers (13; 23; 26). The V protein of simian virus 5 (SV5) for example is capable of blocking the activation of interferon responsive genes in primate cells but not in murine cells (14). This may be the relevant mechanism preventing a productive SV5 infection of mice and even of SCID mice (13). Recently, HRSV, the human equivalent of BRSV, has been reported to be resistant to IFN induced antiviral activity in human cells (2), and from our results we conclude that the HRSV NS proteins are optimized to antagonize the IFN response in human cells and better than in cells of different origin.

In fact, the contribution of the NS proteins to host sensitivity to an RSV infection may explain why these closely related viruses have a strongly limited host range. BRSV and HRSV are capable of entering human, bovine, and murine cells; the different capability of the NS proteins to antagonize the host-specific defense mechanisms may determine whether the virus is eliminated or not. This is also supported by earlier findings. Although the growth of HRSV in primary mouse embryonic (ME) cells was clearly limited, the virus yield was increased after addition of anti-murine IFN serum to the medium and the infection spread to the complete monolayer (26). Furthermore, recombinant BRSVs having their G and F surface proteins replaced by those of HRSV to facilitate their penetration into primate cells were only slightly more competent for replication in chimpanzee than BRSV. However, the infection remained very limited and was not sufficient to induce a protection against an experimental infection with homologous HRSV (6). From our observations we conclude that the low effectiveness of the BRSV NS proteins in antagonizing the defense mechanisms of primates is the primary determinant of the host range.

Therefore, our results bear important implications for the design of effective attenuated RSV live vaccines. The deletion of NS1 or NS2 or of both genes results in over-attenuated viruses unable to escape any interferon response. Furthermore, vaccines may be designed which have the intermediate ability of escaping the bovine and human innate defense mechanisms due to a mutual exchange of the NS proteins between different RSVs, for example BRSV and HRSV, and particularly to generate BRSV and HRSV vaccines. In addition, mutations may be introduced into the NS proteins which only partially abolish the IFN antagonizing activity.

Moreover, the RSV NS1 and/or NS2 proteins or nucleic acid sequences encoding NS1 and/or encoding NS2 according to this invention are also useful for the preparation of pharmaceutical formulations for the reduction of the IFN mediated immune response. In a preferred embodiment, RSV NS1 is used in combination with the NS2 protein for the preparation of a pharmaceutical formulation. The pharmaceutical formulation comprises an effective amount of NS1 and/or NS2 to alter the IFN mediated immune response in an animal or a human, and a pharmaceutically acceptable carrier or diluent. The pharmaceutical formulation may be prepared using conventional techniques. Thus, the pharmaceutical formulation according to the present invention may be prepared by admixing a desired amount of an RSV NS1 and/or NS2 protein or a nucleic acid sequence encoding NS1 and/or a nucleic acid sequence encoding NS2 to a sterile isotonic solution the pH value of which is adjusted to a pH of about 6.0 using an appropriate buffer.

The pharmaceutical formulation according to the present invention may include conventional components e.g. a pharmaceutically acceptable carrier or diluent such as saline, pH regulator, buffer, preservative, and the like. Such components are known to those skilled in the art by whom they may be selected.

The term "IFN" according to the present invention preferably refers to type I interferon, namely interferon α and β.

The term "IFN mediated immune response" herein refers to the immunizing and/or antiviral effects induced by the activity of interferon, particularly interferon α and β, as a response to e.g. a virus infection such as increased expression of MHC glycoproteins, activation of antiviral mechanisms such as destruction of virus-infected cells, or inhibition of virus replication.

"Reduction of the IFN mediated immune response" means that the immunizing and/or antiviral effects are reduced which are induced by the activity of interferon, particularly interferon α and β, for example as a response to virus infection such as increased expression of MHC glycoproteins, activation of antiviral mechanisms such as destruction of virus-infected cells, or inhibition of virus replication.

"IFN antagonizing activity" according to the present invention means that the immunizing and/or antiviral effects are reduced or abolished which are induced by the activity of interferon, particularly interferon α and β, for example as a response to virus infection such as increased expression of MHC glycoproteins, activation of antiviral mechanisms such as destruction of virus-infected cells, or inhibition of virus replication.

The terms "modified" or "altered" according to the present invention relate to the wild type which is used as a reference.

"Nucleic acid sequence" as used herein means any continuous sequence of nucleotide bases and may consist of ribonucleic acid or deoxyribonucleic acid. Preferably, the nucleic acid sequence is cDNA.

A "nucleic acid sequence encoding NS1 and/or NS2 homologous or heterologous to an RSV" means that the nucleic acid sequence encoding NS1 and/or NS2 is derived from the same or a different RSV species or from another virus of the genus *Pneumovirus*, e.g. PVM.

Modifications within a protein sequence of RSV NS1 or RSV NS2 include single or multiple amino acid substitutions, deletions, and insertions. Preferably, the modifications have no effect on the biological activity of the proteins in reducing the IFN mediated immune response or antagonizing IFN. Amino acid insertion variants according to the present invention include amino and/or carboxy terminal fusions and internal sequence insertions of single or multiple amino acids. Amino acid insertion variants are those wherein one or more amino acids are introduced into a specific site within the protein; random insertion, however, is also possible in combination with appropriate screening of the resulting product. Deletion variants are characterized by deletion of one or more amino acids from the sequence. Substitution amino acid variants are those wherein at least one residue is removed from the sequence and replaced by another residue at the same site. Preferably, the sequence of the unmodified NS1 or NS2 protein has a homology to the wild type of at least 40%, preferably at least 50%, more preferably at least 80% or at least 90%, particularly 95%.

Preferred modifications are present in positions which are not conserved between species. Preferably, a modification of this type comprises the substitution of one amino acid by another having a similar size and polarity. With respect to the type of the possible substitutions made there may first be used analyses of the frequency of amino acid substitutions between homologous proteins in different organisms. Based on these analyses conservative substitutions are defined as substitutions within the groups listed below:

1. small aliphatic, apolar or weakly polar: Ala, Ser, Thr (Pro, Gly)
2. negatively charged and the amides thereof: Asn, Asp, Glu, Gln
3. positively charged: His, Arg, Lys
4. large aliphatic, apolar: Met, Leu, lie, Val (Cys)
5. large aromatic: Phe, Tyr, Trp.

Three amino acids are written in brackets due to their specific role in protein architecture. Gly is the only amino acid without side chain and therefore confers flexibility to the peptide chain. Pro has an unusual geometry strongly limiting chain flexibility. Cys may be involved in disulfide bonds.

Furthermore, modifications as detailed above may be introduced into the protein sequence of RSV NS1 or RSV NS2 resulting in an enhancement or reduction of the biological activity of the proteins to reduce the IFN mediated immune response or to antagonize IFN.

BRIEF DESCRIPTION OF THE DRAWINGS

FIG. 3. NS deletion mutants are more attenuated in MDBK cells than in BSR cells. Almost confluent BSR T7-5 (A) and MDBK (B) monolayers were infected in a MOI of 0.01 with BRSV (black circles), BRSV ΔNS1 (white squares), BRSV ΔNS2 (black triangles), or BRSV ΔNS1/2 (white circles). Infectious virus titers were determined on every two days as described in the Example section. Starting with the sixth day, the replication of all mutants in BSR cells and the replication of wt BRSV in MDBK cells resulted in massive cell destruction. The values were obtained from two independent experiments each of which was performed in triplicate. Bars indicate the standard deviation.

FIG. 4. Supernatants of virus-infected MDBK cells or infected macrophages inhibit the growth of the BRSV NS deletion mutants in co-cultured Vero cells. The rationale of the co-cultivation experiments is shown schematically in (A). MDBK cells or LPS-stimulated bovine macrophages were infected with BRSV in a MOI of 1, seeded into Nunc "Anopore Membrane" cell culture inserts, and cultured with Vero "responder" cells infected by wt BRSV, BRSV ΔNS1, BRSV ΔNS2, or BRSV ΔNS1/2. After three days, the inserts were removed and the infectious virus titers of the Vero cells were determined. The results in (B) are shown as % inhibition including the standard deviation and as times reduction (of the means values) as compared to controls obtained with uninfected MDBKs or uninfected, unstimulated macrophages. The values are obtained from 6 (MDBKs) and 4 (macrophages) co-cultivation experiments.

FIG. 6. All BRSV NS deletion mutants are type I IFN sensitive. Vero cells infected with BRSV (black circles), BRSV ΔNS1 (white squares), BRSV ΔNS2 (triangles), or BRSV ΔNS1/2 (white circles) in a MOI of 0.1 were incubated with recombinant IFN alpha A/D (A) or IFN beta (B) in the amounts indicated. Infectious virus titers were determined 4 days following infection.

FIG. 8. Increased IFN resistance of rabies viruses (RV) in cells infected with NS1 and NS2 expressing RVs. Vero (A) or MDBK cells (B) were infected with RV SAD VB, SAD VB-NS1, or SAD VB-NS2 or co-infected with SAD VB-NS1 and SAD VB-NS2. Immediately following infection the cultures were treated with IFN alpha A/D in the amounts indicated. Infectious virus titers were determined 2 days following infection. The results represent the mean values from at least four independent experiments and error bars indicate the standard deviations.

FIG. 9. Duplicate samples of $1 \times 10^5$ Hep2 cells each were infected with the different HRSV isolates for 1 hour (MOI=0.1) in 0.5 ml of DMEM w/o FCS whereafter each sample received 0.5 ml+5% FCS. Afterwards the infected cells were seeded in 4 cm² tissue culture plates. After 1, 2, 3, and 4 days a current value was removed for each virus isolate, the virus was released by freezing/thawing and the titers of the different clinical isolates depending on the infection period were determined by titration. The pfu/ml was determined by counting after staining of the infected cells with an antibody against RSV-F.

FIG. 10. Duplicate samples of $1 \times 10^5$ Hep2 cells each were infected with the different HRSV isolates for 1 hour (MOI=0.1) in 0.5 ml of DMEM w/o FCS and afterwards seeded in 4 cm² tissue culture plates. 0, 150, 500, 10,000 U/ml of recombinant type I IFN A/D were suspended in another 0.5 ml DMEM+5% FCS and added after 30 min.

After an incubation period of 72 hours, the virus was released by freezing/thawing and the titers of the different clinical isolates depending on the amount of IFN added were determined by titration. The pfu/ml was determined by counting after staining of the infected cells with an antibody against RSV-F.

Figure 11:
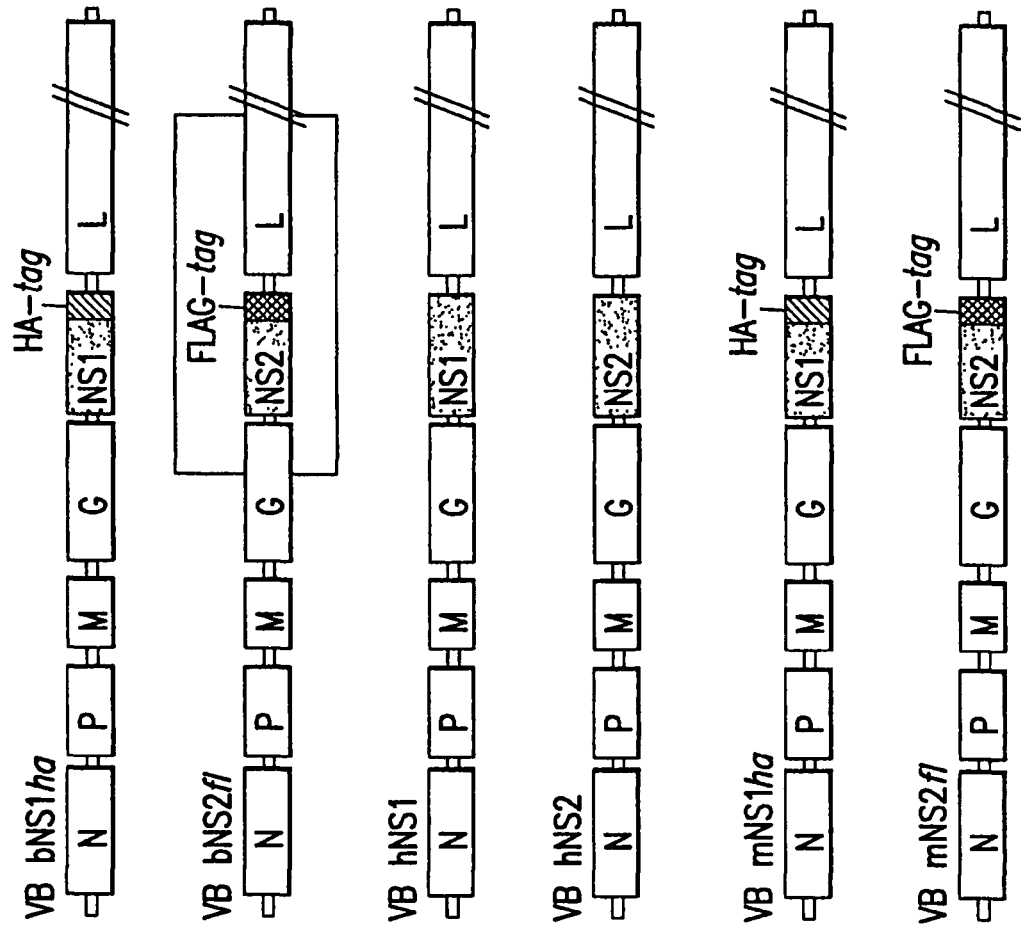

FIG. 11, Organization of recombinant rabies viruses (RV) harboring HRSV NS1 or HRSV NS2 or genetically labeled BRSV NS1, BRSV NS2, PVM NS1 or PVM NS2 ORFs between the RV G and L genes.

Figure 12:
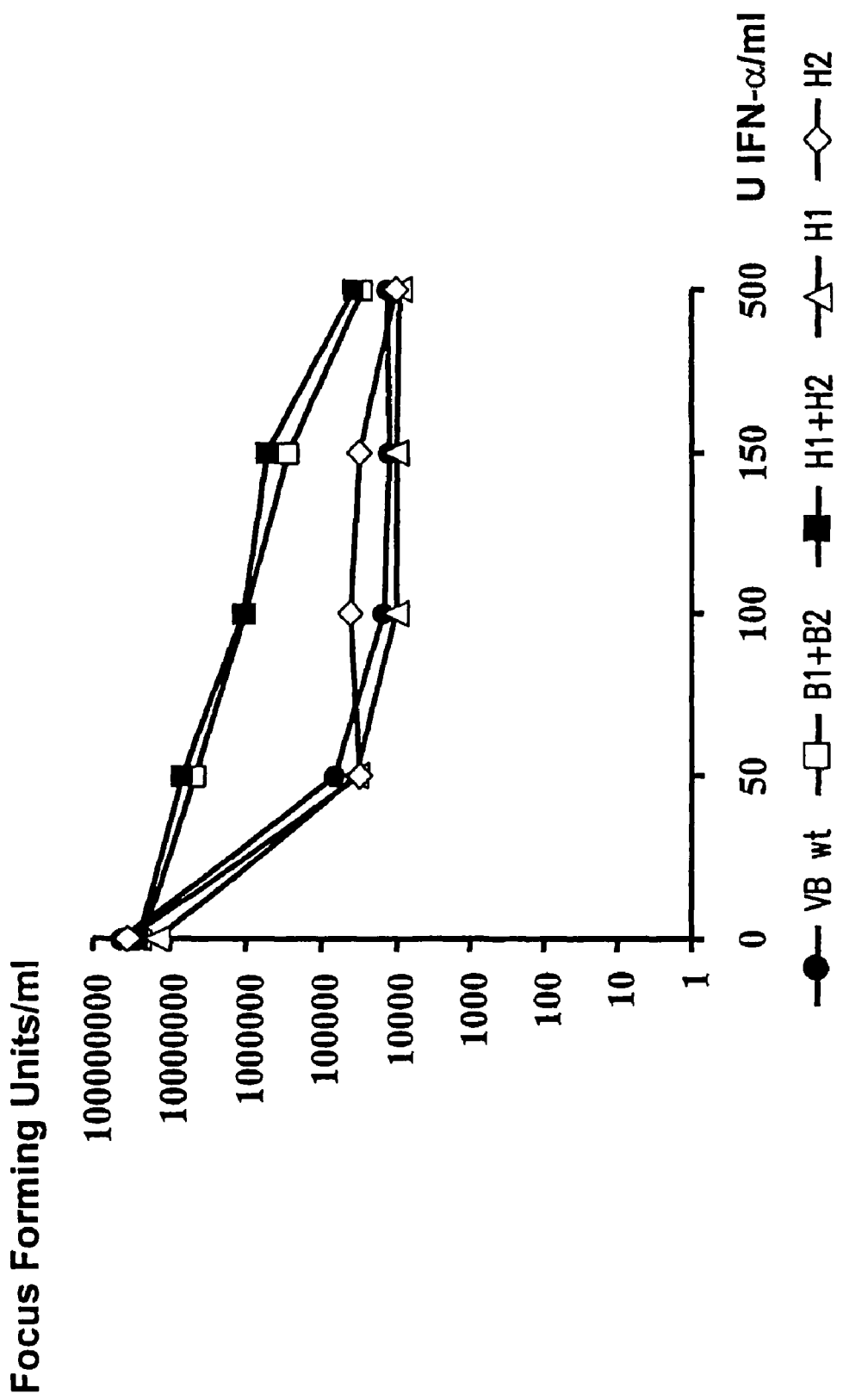

FIG. 12. Increased IFN resistance of rabies viruses (RV) infected with RVs expressing NS1 and NS2. MDBK cells were infected with RV SAD VB, SAD VB-hNS1, or SAD VB-hNS2 or co-infected with SAD VB-hNS1 and SAD VB-hNS2 or with SAD VB-bNS1 and SAD VB-bNS2. Immediately following infection the cultures were treated with IFN alpha A/D in the amounts indicated. Virus titers were determined 2 days following infection. The results represent the mean values from at least four independent experiments and error bars indicate the standard deviations.

Figure 13:
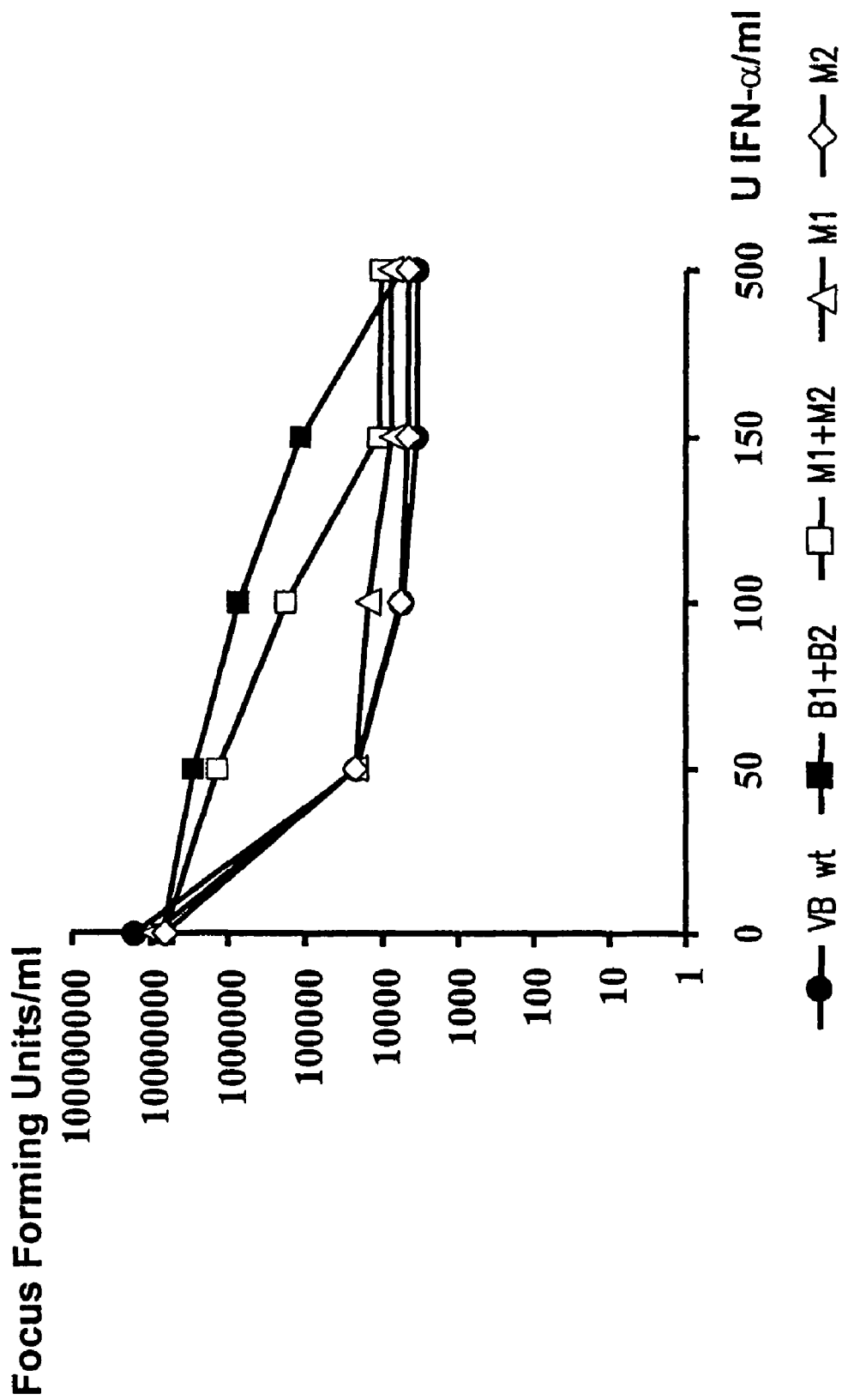

FIG. 13. Increased IFN resistance of rabies viruses (RV) infected with RVs expressing NS1 and NS2. MDBK cells were infected with RV SAD VB, SAD VB-mNS1, or SAD VB-mNS2 or co-infected with SAD VB-mNS$_1$ and SAD VB-mNS2 or with SAD VB-bNS1 and SAD VB-bNS2. Immediately following infection the cultures were treated with IFN alpha A/D in the amounts indicated. Virus titers were determined 2 days following infection. The results represent the mean values from at least four independent experiments and error bars indicate the standard deviations.

Figure 14:
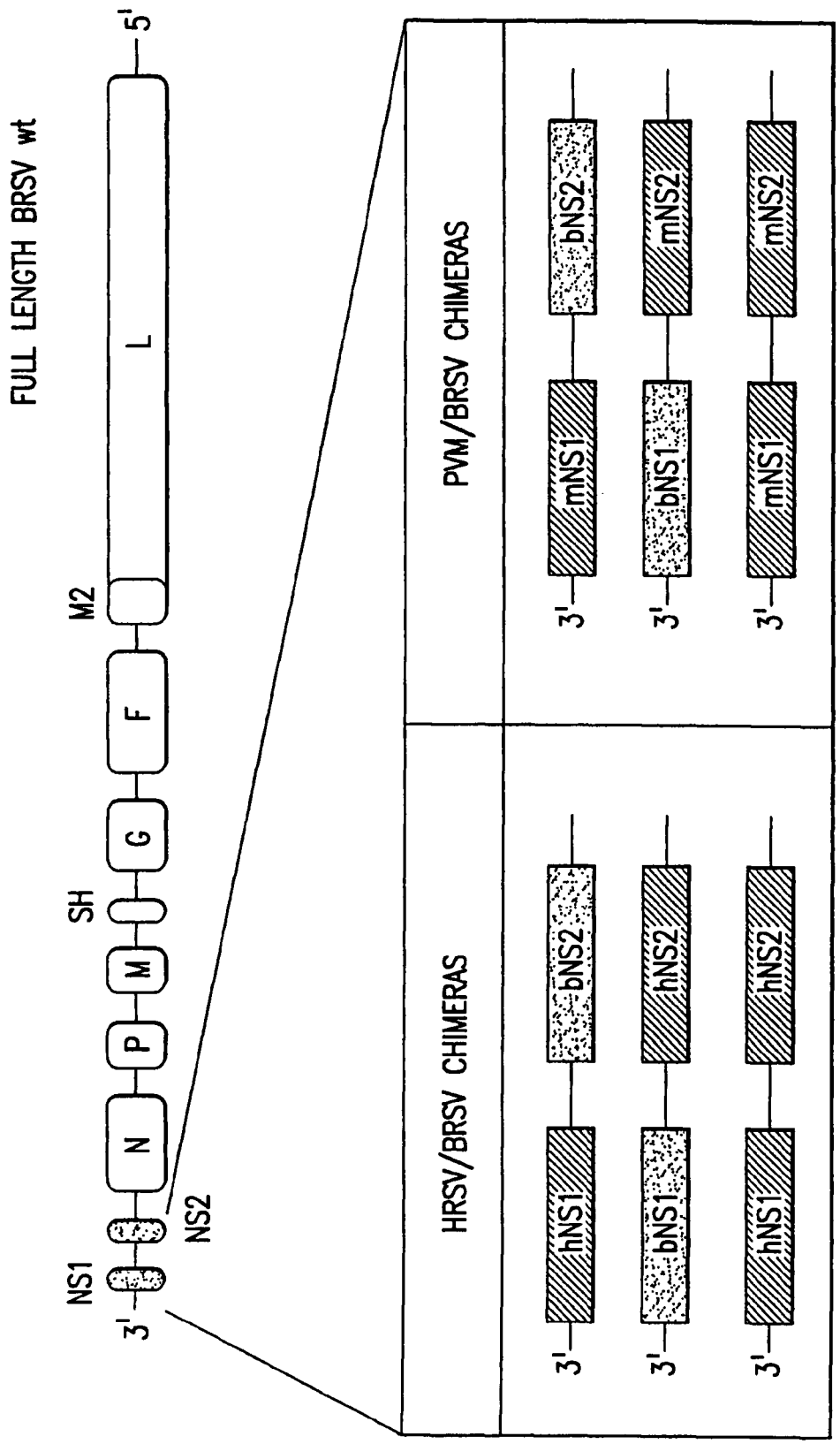

FIG. 14. Organization of the chimeric BRSVs harboring heterologous NS genes.

Figure 15:
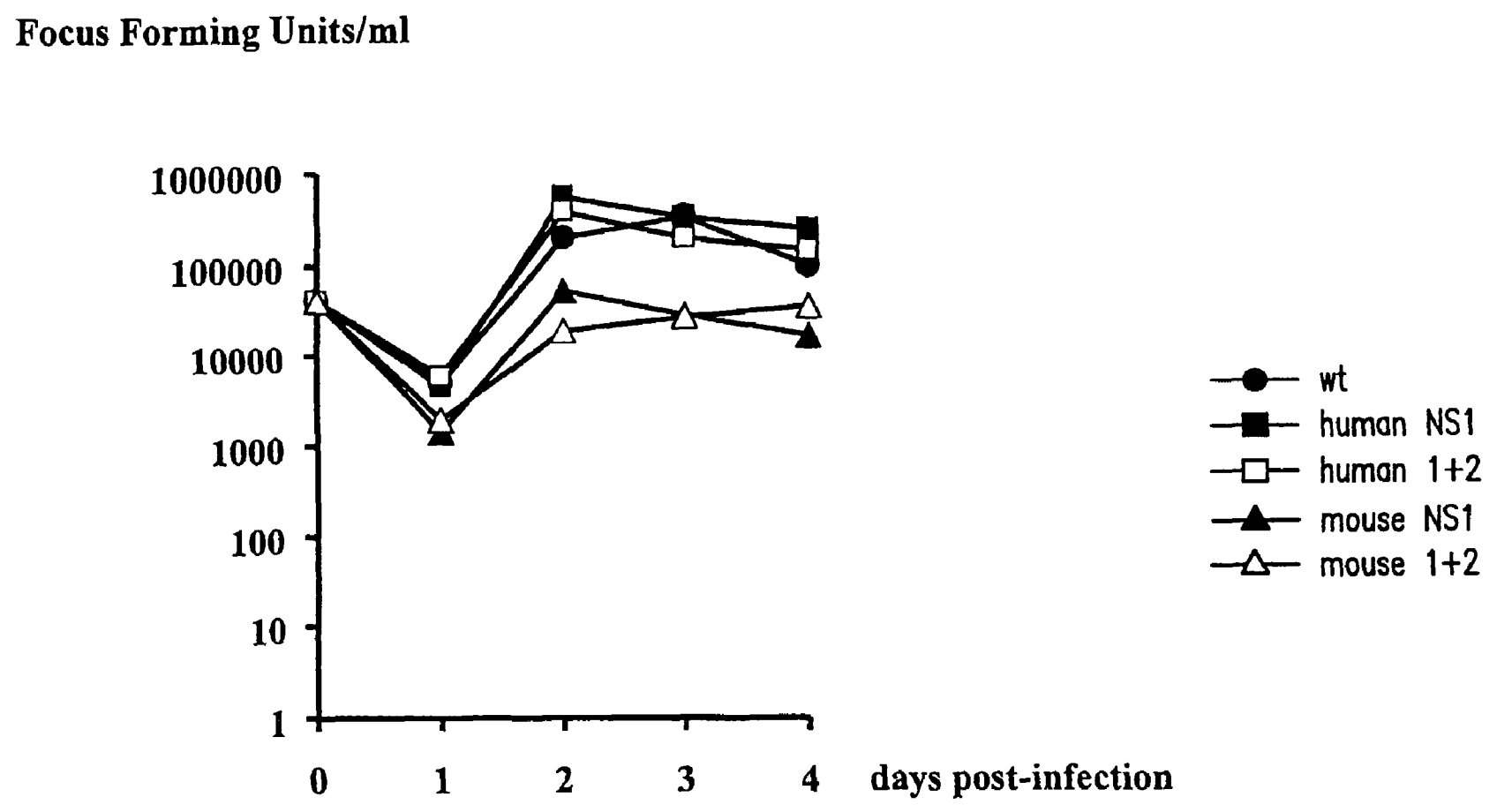

FIG. 15. The PVM/BRSV chimeras are slightly attenuated on Vero cells. Vero cells were infected with BRSV wt (black circles), BRSV hNS1bNS2 (dark gray squares), BRSV hNS1hNS2 (light gray squares), BRSV mNS1bNS2 (dark gray triangles), and BRSV mNS1mNS2 (light gray triangles) in a MOI of 0.1. Infectious virus titers were determined on four successive days. The values were obtained from at least two independent experiments.

Figure 16:
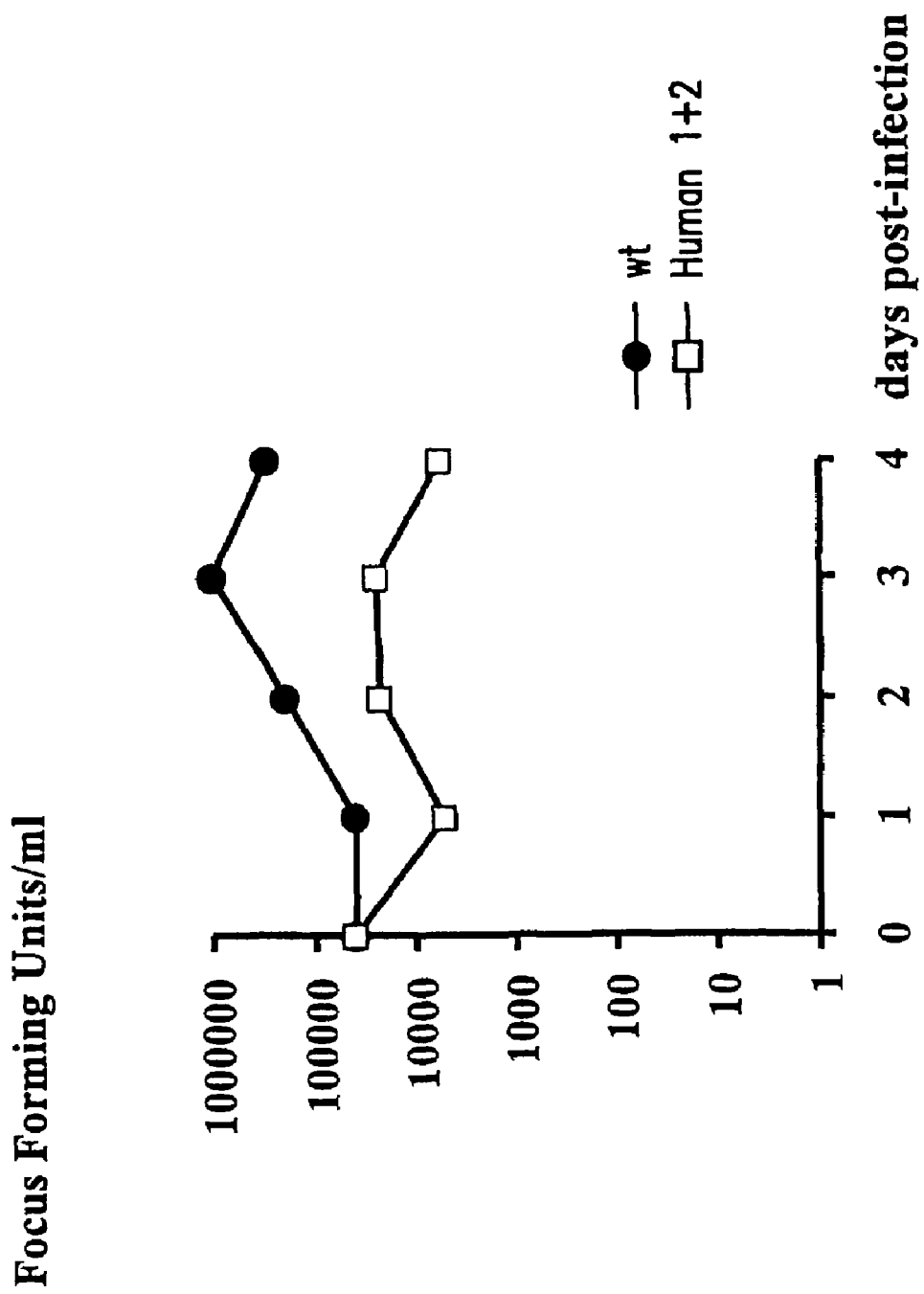

FIG. 16. The growth of BRSV hNS1hNS2 is attenuated on MDBK cells. MDBK cells were infected with BRSV wt (black circles) and BRSV hNS1hNS2 (light gray squares) in a MOI of 0.1. Infectious virus titers were determined on four successive days. The values are mean values obtained from at least two independent experiments.

FIG. 17. BRSV hNS1hNS2 is sensitive to IFN type I on MDBK cells. Vero (A) and MDBK (B) cells were infected with BRSV wt (black circles) and BRSV hNS1hNS2 (light gray squares) in a MOI of 0.1 and afterwards incubated with recombinant IFN alpha A/D in the amounts indicated. Infectious virus titers were determined 3 days following infection. The values were obtained from at least two independent experiments.

FIG. 18. Comparison of the amino acid sequences of the NS1 (FIG. 18A) and NS2 proteins (FIG. 18B) of HRSV (hNS1; hNS2), BRSV (bNS1, bNS2), and PVM (mNS1, mNS2); GenBank accession No. U35030 (HRSV Long strain), AF092942 (BRSV strain A Tue 51908), and D10331 (PVM).

The following Examples are presented for the purpose of illustrating different embodiments of the invention and are not intended to limit the present invention in any way.

EXAMPLES

Example 1

Construction and Rescue of BRSV Deletion Mutants Lacking NS Genes

The recombinant BRSV (rBRSV) is derived from BRSV strain A51908 (American Type Culture Collection (ATCC) (33), variant Atue51908 (GenBank acc. No. AF092942)), and was cultured in MDBK cells as already described (5). Cloning of the full length cDNA of BRSV strain Atue51908 (GenBank acc. No. AF09294) and construction of plasmids enabling the T7 RNA polymerase mediated transcription of the BRSV full length antigenomic RNA or of the antigenomic RNA without NS2 gene (PBRSV ΔNS2) has been described elsewhere (5).

Figure 1A:
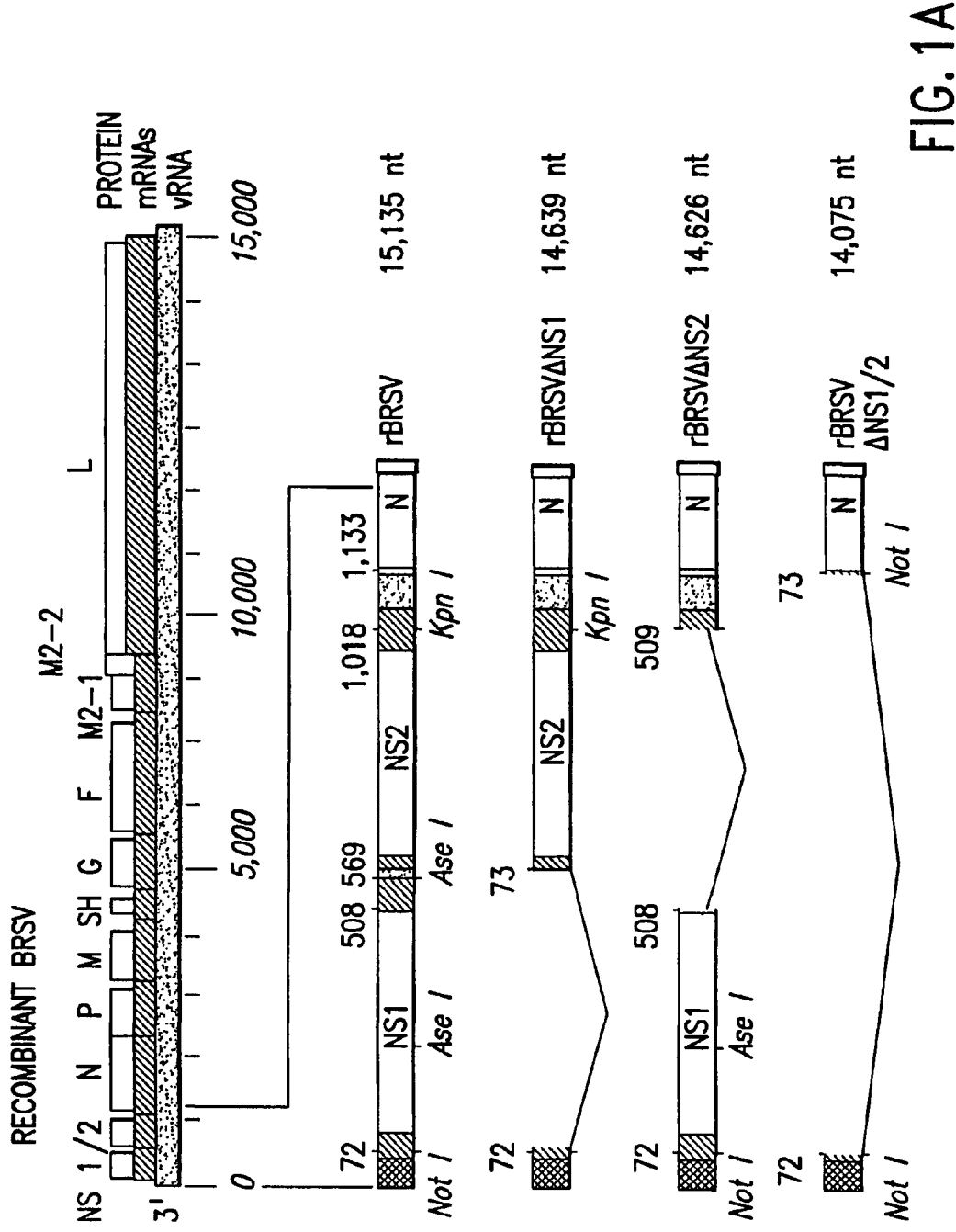
FIG. 1. (A) Schematic representation of the genomes of recombinant BRSVs. The position of the transcripts (grey bars) and protein coding regions (white bars) are shown in relation to the viral genome (vRNA) (black bars). The enlargement compares the organization of the full length virus and the NS deletion mutants. The leader RNA is indicated by horizontal lines; the relative positions of the respective nucleotides and restriction sites used for cloning are indicated. (B) Organization of recombinant rabies viruses (RV) carrying genetically labeled BRSV NS1 or BRSV NS2 ORFs between the RV G and L genes.
Figure 1B:
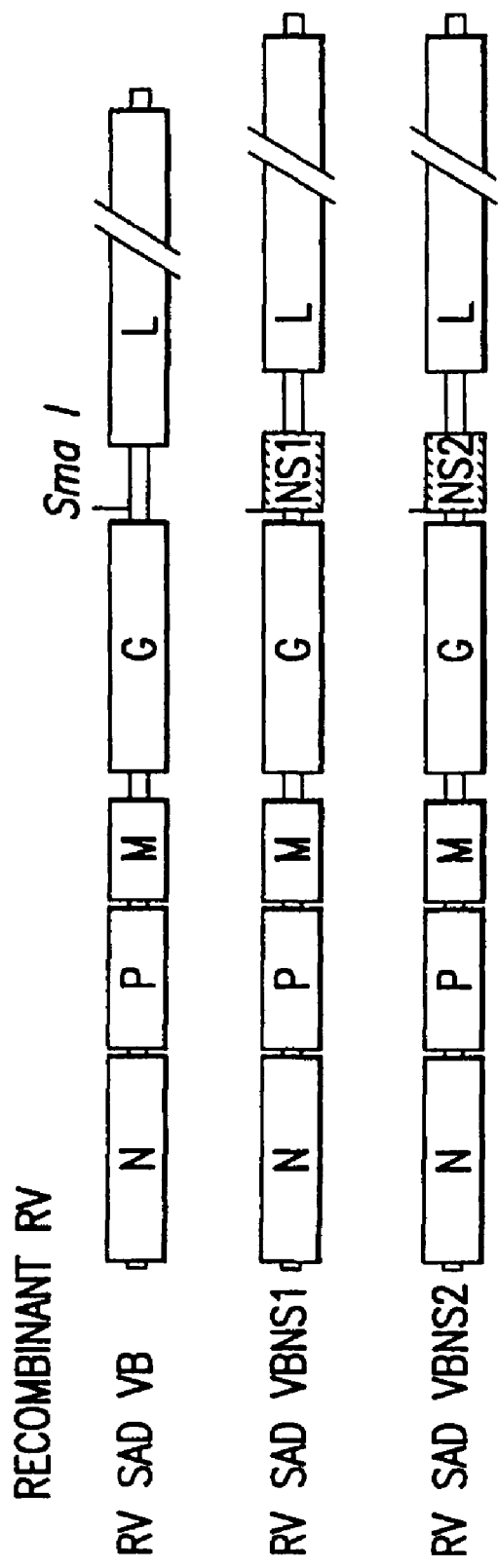

Constructs lacking the $NS_1$ gene (PBRSV ΔNS1) or both genes NS1 and NS2 (PBRSV ΔNS1/2) were also generated on the basis of pBRSV. The NS1 gene was removed from pBRSV by cutting with NotI and AseI, filling in with Klenow polymerase and subsequent religation. In this manner pBRSV ΔNS1 was obtained. To generate the double deletion mutant pBRSV ΔNS1/2 a 0.6 kb PCR fragment was amplified which comprises part of the N gene. For this purpose, primer NNot(+) (5'-TAGGCGGCCGCAAAAATGGCTCTTAGC-AAGGTG-3') (SEQ ID NO:1) was used containing a NotI restriction site (underlined) upstream of the N start codon as well as the reverse primer Nstu(-) (5'-TCCTTTG-TATCGTTTCATTTC-3') (SEQ ID NO:2) corresponding to nt 1735-1715 of rBRSV downstream of the unique StuI restriction site (rBRSV position 1671). After deletion of the NS1 and NS2 genes and a portion of the N gene from pBRSV by digestion with NotI (rBRSV position 72) and StuI (rBRSV position 1671), the StuI restricted PCR fragment was used to replace the deleted sequences (FIG. 1).

Compared to the sequence of the recombinant wt virus rBRSV the NS1, NS2 and NS1/NS2 deletion mutants lack 496, 509 and 1060 nucleotides, respectively. In all constructs the transcription of the 3'-terminal gene is induced by the original leader/NS1 transcriptional start signal (FIG. 1).

Viable recombinant viruses rBRSV, rBRSV ΔNS1, rBRSV ΔNS2, and rBRSV ΔNS1/2 could be obtained from the respective cDNA constructs in BSR T7/5 cells (5) expressing T7 RNA polymerase following transfection (CaPO$_4$ protocol; Mammalian Transfection Kit, Stratagene) of T7 promoter-controlled plasmids with the respective virus cDNA (10 μg). Plasmids encoding the BRSV proteins N and P (PTITB-N and pTITB-P, 4 μg per plasmid), and L and M2 (PTITB-L and pTITB-M2, 2 μg per plasmid) were co-transfected with each virus cDNA into about 10$^6$ BSR T7/5 cells stably expressing phage T7 RNA polymerase (5). After 4 hours, the transfection medium was removed and BHK-21 medium (Gibco) containing 5% FCS was added. Cells transfected with BRSV cDNA were diluted every 5 days in a ratio of 1:3 until a cytopathogenic effect could be observed.

In all cases including the NS1/2 double mutants co-transfection of the support plasmids encoding the BRSV N, P, L, and M2 proteins resulted in the formation of syncytia. After dilution of the transfected cells in a ratio of 1:3 and occurrence of a clear cytopathogenic effect the viruses were harvested.

For the preparation of virus stock solutions 80% confluent MDBK and Vero cells were infected in a multiplicity of infection (MOI) of 0.1 in Dulbecco's minimal essential medium (DMEM) without serum. After adsorption for one hour the inoculum was removed and the cells were incubated at 37° C. in DMEM supplemented with 2.5% FCS in a 5% CO$_2$ atmosphere until a clear cytopathic effect (CPE) was observed. The viruses were released by freezing and subsequent thawing. The virus titers on Vero cells were determined by dilution series in microtiter plates followed by counting of infected foci. For this purpose the foci were stained by indirect staining using an antibody against the F fusion protein (obtained courtesy from J. A. Melero, Madrid). Preparation of virus stock solutions of the NS deletion mutants was carried out on Vero cells infected in a MOI of 0.1. It took 3 days in the case of rBRSV and 5 days in the case of NS deletion mutants until a clear CPE was observed after infection of Vero cells in a MOI of 0.1.

Example 2

Growth of the Ns Deletion Mutants

Figures 3A, 3B:
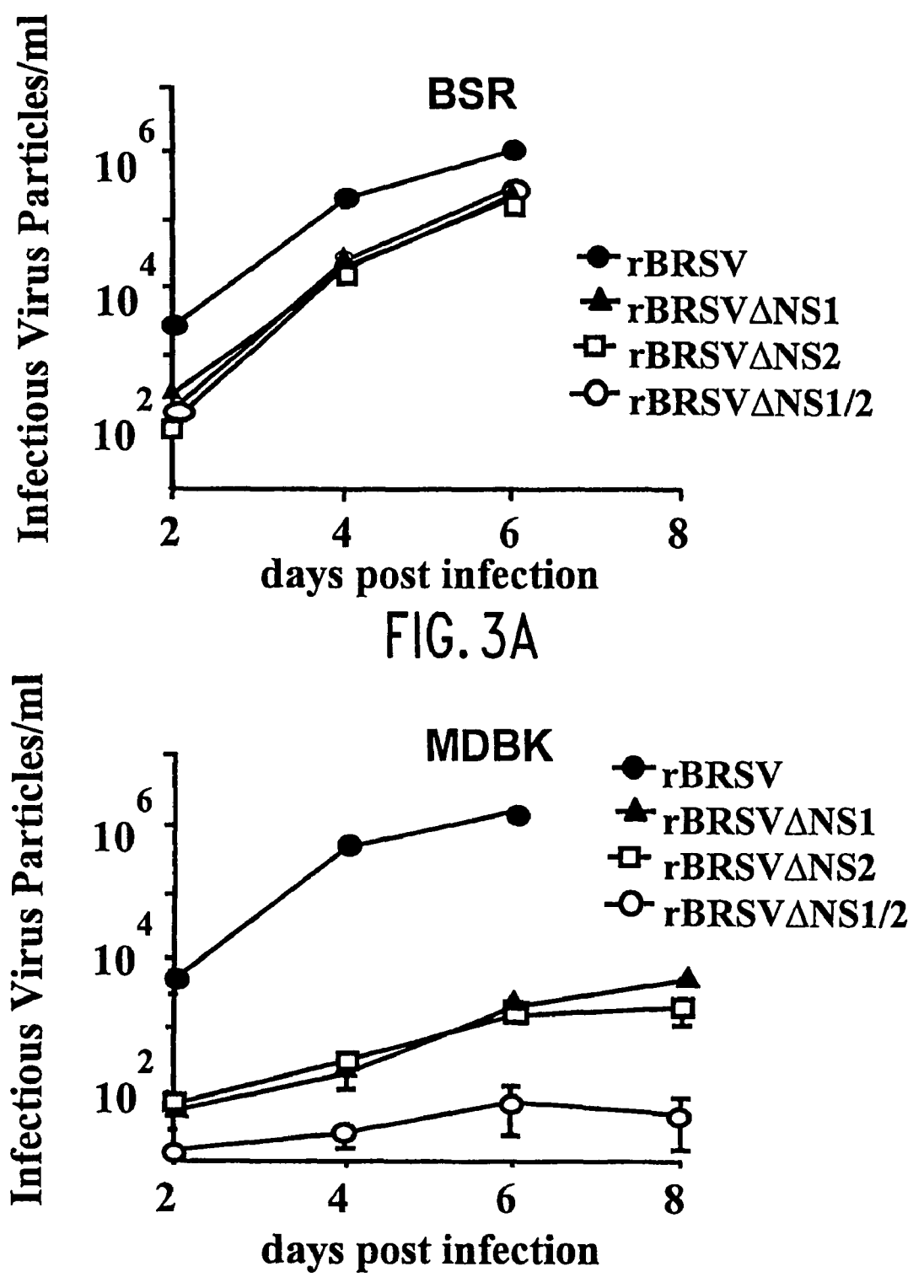

The growth characteristics of the viruses were first analyzed in the cell line BSR T7/5 derived from BHK cells which was used to rescue the viruses. In contrast to the parental full length virus all three mutants were attenuated indicating a contribution of both NS proteins to virus replication. Interestingly, no obvious differences could be observed with respect to the distribution of the viruses in infected cells and the final titers between the single and the double deletion mutant. All mutants attained infectious titers of 2×10$^5$ pfu after infection of BSR T7/5 cells in a MOI of 0.1 and a subsequent incubation period of 6 days. The parental virus, however, reached up to 1×10$^6$ pfu (FIG. 3A). Similar results with slightly enhanced titers were achieved by infection of Hep2 or Vero cells the latter being the preferred cell line for the culturing of HRSV.

Subsequently, a cell line of bovine origin, MDBK, was used which optimally supports the growth of wt BRSV (5).

Indeed, slightly enhanced BRSV titers of $2\times10^6$ pfu could be achieved after 6 days of infection (FIG. 3B). Surprisingly, however, growth of the deletion mutants in this cell line was strongly affected. The single deletion mutants ΔNS1 and ΔNS2 attained titers of only $3\times10^3$ pfu after 6 days which is 100 times lower than in BSR cells. The double deletion mutant ΔNS1/2 was unable to detectably multiply within the first 6 days of infection. Not before the cells were diluted and incubated for another 8 days a virus titer of $2\times10^2$ could be obtained. Although MDBK cells represent the optimal host cell for wt BRSV they obviously are not permissive for all NS deletion mutants while BSR and Vero cells being suboptimal host cells for wt BRSV exhibit relatively good support of the growth of the NS deletion mutants.

Example 3

Northern Hybridization with Rna of BRSV Deletion Mutants Lacking NS Genes

For Northern hybridizations the RNA was isolated from cells infected with rBRSV or the NS deletion mutants.

Vero cells were infected with the recombinant viruses rBRSV, rBRSV ΔNS1, rBRSV ΔNS2, and rBRSV ΔNS1/2 in a MOI of 0.1 and total RNA was isolated after a strong CPE was observed (for rBRSV after 3 days, for NS deletion mutants after 5 days). The RNA was separated by denaturing gel electrophoresis, transferred onto nylon membrane (Duralon-UV, Stratagene), and bound to the membrane by means of UV irradiation. NS1, NS2, and N gene specific DNA probes of about 500 nt in length were labeled with ($\alpha$-$^{32}$P) dCTP (3,000 Ci/mmol, Amersham) by nick translation (Nick-translation kit, Amersham). The hybridized filters were exposed to Kodak Biomax MS films using intensifying screens or were evaluated by means of phosphor imaging (Storm, Molecular Dynamics).

Figure 2:
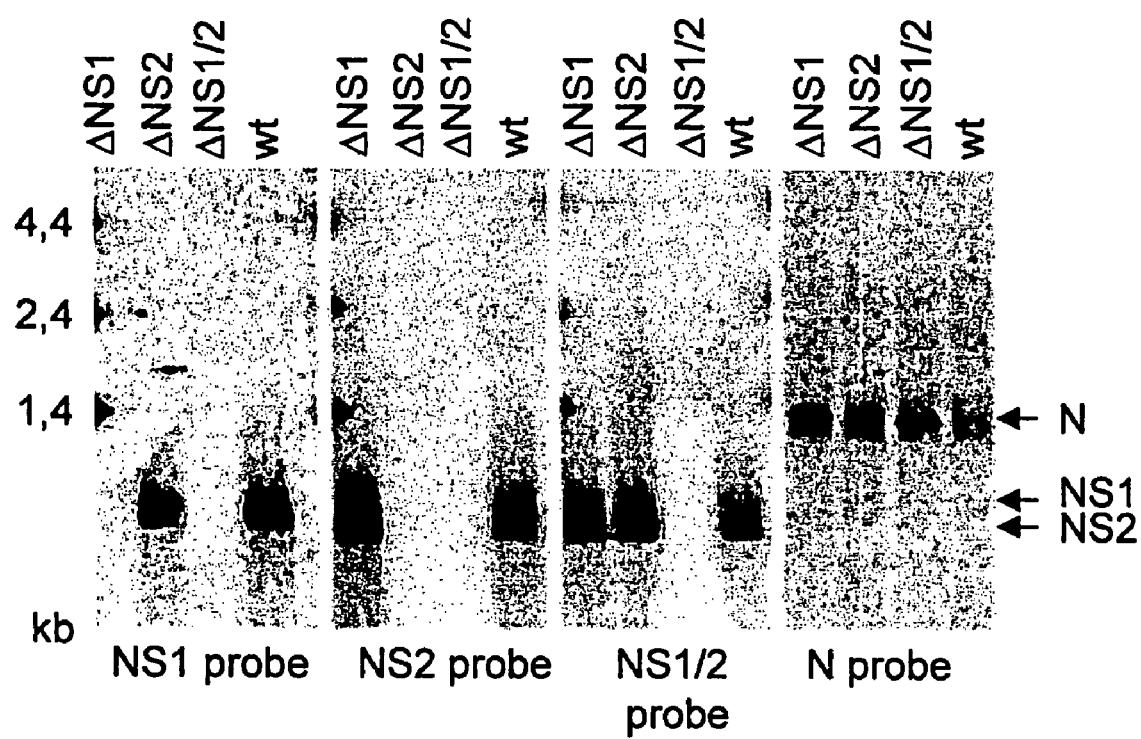
FIG. 2. Absence of NS1 and NS2 transcripts in recombinant BRSV. Full length RNA from BSR cells infected by the viruses indicated were isolated 2 to 4 days post infection and analyzed by Northern hybridization using probes comprising the NS1, NS2, NS1 to NS2, and N genes. The NS1, NS2, and N mRNAs are indicated.

Similar transcript patterns were observed for all viruses wherein the viruses differed only in the presence or absence of RNAs specific for NS1 and NS2 (FIG. 2). As already observed for BRSV and HRSV NS2 deletion mutants (5; 43) similar amounts of N mRNA and genomic RNA were present in all infected cells regardless of the recombinant used. Therefore, the NS proteins rather have an effect on RNA synthesis in general instead of affecting distinct steps in RNA replication or transcription.

Example 4

Soluble Factors Produced By MDBK Cells and Bovine Macrophages Affect the Growth of NS Deletion Mutants To identify cellular factors responsible for the obvious selective inhibition of the growth of NS deletion mutants in MDBK cells it was first examined whether soluble molecules produced by MDBK cells are capable of limiting the growth of NS deletion mutants. For this purpose, MDBK cells and Vero cells were co-cultured in devices enabling the separation of the two cell cultures by a membrane which is virus impermeable but permeable for soluble factors (FIG. 4A). MDBK cells in the upper dish were used as effector cells while Vero cells in the lower dish served as responder cells.

Vero responder cells in suspension were either mock infected or infected with rBRSV ΔNS1, rBRSV ΔNS2, or rBRSV ΔNS1/2 in a MOI of 0.1 in DMEM without FCS for one hour. After washing $5\times10^5$ cells each in DMEM containing 2.5% FCS were seeded in 6 well dishes. MDBK effector cells or bovine macrophages stimulated with 10 μg/ml LPS (Sigma) over night were infected in suspension with rBRSV in a MOI of 1 for 1 hr. After washing $1\times10^6$ cells were seeded in 25 mm cell culture inserts equipped with a 200 nm Anopore membrane (Nunc) and placed into the dishes containing the infected Vero "responder" cells. After co-culturing for three days the membrane inserts were removed and the virus titer of the Vero cells was determined as described in Example 1.

At least five independent co-cultivation experiments were performed. Uninfected MDBK effector cells or BSR cells used as a negative control showed no inhibitory effect on the growth of wt BRSV or the NS deletion mutants in Vero responder cells. Co-cultivation with BRSV-infected MDBK cells (MOI =1) resulted in a weak but reproducible inhibition of the NS deletion mutants while the growth of wt BRSV was unaffected (FIG. 4B). The most pronounced effect was observed with the NS1/2 double deletion mutant. In this case the titers were reduced about 7fold in the presence of infected MDBK cells as compared to uninfected MDBK cells. The titers of the single deletion mutants rBRSV ΔNS1 and rBRSV ΔNS2 in this case were reduced by 2 and 4fold, respectively.

Since the supernatants of uninfected MDBK cells were unable to affect growth of the deletion mutants in Vero responder cells it was assumed that the effective MDBK factors were induced by virus infection. Not only infections by wt BRSV but also with a plurality of BRSV deletion mutants including rBRSV ΔNS1/2 and a mutant with deleted SH and G genes (rBRSV ΔSH/G; unpublished) resulted in secretion of the effective factors. In addition it could be demonstrated that infection with a different RNA virus, rabies virus, also resulted in an induction of effective factors in MDBK cells. These results strongly suggested an induction of the antiviral state in Vero responder cells mediated by cytokin, particularly by interferon.

To study the cytokins involved in more detail bovine macrophages were used as effector cells. Bovine macrophages were isolated from the blood of a cow and a calf using Ficoll gradient centrifugation (Lymphoflot, Biotest, Dreieich) at 1,500 rpm and adsorption of the mononuclear cell fraction to the bottom of the cell culture flask. After incubation over night the non-adherent cells were removed by washing three times with RPMI (Gibco) without FCS. The remaining adherent cells (90-95% CD14 positive) were incubated in RPMI containing 10% FCS at 37° C. and 5% $CO_2$. Isolated bovine macrophages were stimulated with LPS over night and co-cultured with Vero cells as described above.

After incubation with stimulated, virus-infected or unstimulated macrophages the amounts obtained of full length rBRSV remained unchanged. In contrast to the unstimulated and uninfected macrophage control, however, a 30 to 50 fold reduction was observed for the NS deletion mutants (FIG. 4B). Also stimulation of the macrophages only with LPS without subsequent virus infection was sufficient to cause an about 10 fold reduction in rBRSV ΔNS1/2. Since stimulated macrophages are known to be producers of type I interferon these experiments indicate an involvement of IFN alpha and/or beta in inhibiting the growth of BRSV NS deletion mutants.

Example 5

Deletion of the NS Genes Renders BRSV Type I Interferon Sensitive

It could be demonstrated by means of FACS analysis that the Vero cells used as responder cells in the co-cultivation experiments (see Example 4) express the interferon type I receptor alpha subunit (IFNAR2) (44). To study whether IFN alpha and/or beta produced by infected MDBK cells or macrophages mediates the inhibitory effect on the NS deletion mutants Vero responder cells were infected with rBRSV ΔNS1/2, rBRSV ΔNS2, or rBRSV ΔNS1/2 and afterwards treated with a monoclonal antibody blocking IFNAR2 (PBL Laboratories). Treatment of the responder cells was performed immediately after infection by incubating the cells for 1 hr with 5 µg/ml of a neutralizing mouse anti-human interferon alpha/beta receptor chain 2 (CD118) antibody (PBL Biomedical Laboratories) or with 5 µg/ml of a control antibody recognizing TNFRI or MHC class I molecules. After dilution of the cells into six well dishes the cells were kept in 1 µg/ml of the respective antibodies and incubated in the presence of infected MDBK effector cells for three days.

Figure 5:
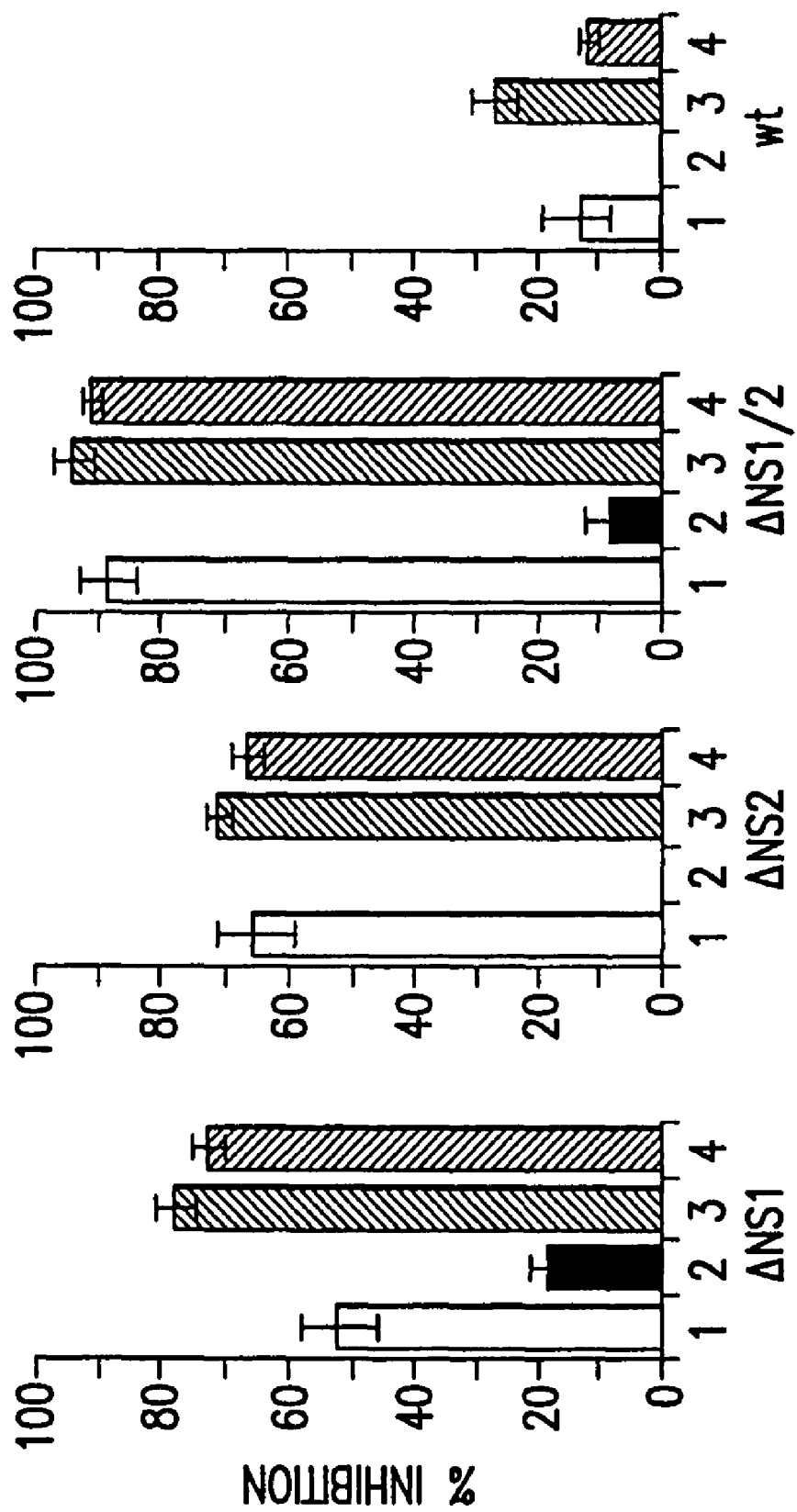
FIG. 5. An interferon alpha receptor (IFNA-R2) monoclonal antibody (#2) neutralizes the effect of the inhibitory factor produced by MDBKs or macrophages. Vero "responder" cells infected with rBRSV ΔNS1, rBRSV ΔNS2, rBRSV ΔNS1/2, or wt rBRSV in a MOI of 0.1 were each incubated with 5 μg/ml of a monoclonal antibody against IFNAR2 (#2), MHC I (#3), TNF-R1 (#4), or in the absence of antibody (#1) for three hours. Co-cultivation with infected MDBK cells (see rationale of the experiment in FIG. 4) was performed in the presence of 1 μg/ml of the respective antibody. The titer was determined in six (#1 and #2) or two experiments (#3 and #4). Bars indicate the standard deviation.

While an inhibition of the NS deletion mutants was observed in the cell cultures containing control antibodies or without antibody the inhibitory effect was almost completely abolished in the cells treated with IFNAR2 antibody (FIG. 5). Due to this result the induction of an antiviral state in Vero responder cells can be attributed exclusively to the type I interferons produced by MDBK cells or macrophages.

Recombinant human type I interferons were then used to directly analyze the behavior of wt BRSV and BRSV mutants in IFN stimulated cells. To study the effect of type I interferon on the replication of BRSV and the NS deletion mutants Vero or MDBK cells were infected with the different viruses in a MOI of 0.1 as described above and seeded in six well dishes in DMEM containing 2.5% FCS. Recombinant universal type I interferon (human interferon alpha A/D) or human interferon beta (PBL Biomedical Laboratories) were added directly after seeding up to a concentration of 15,000 U/ml. The virus titers were determined after an incubation period of three days by means of dilution series and indirect staining of infected cells with an antibody against the F fusion protein.

Figures 6A, 6B:
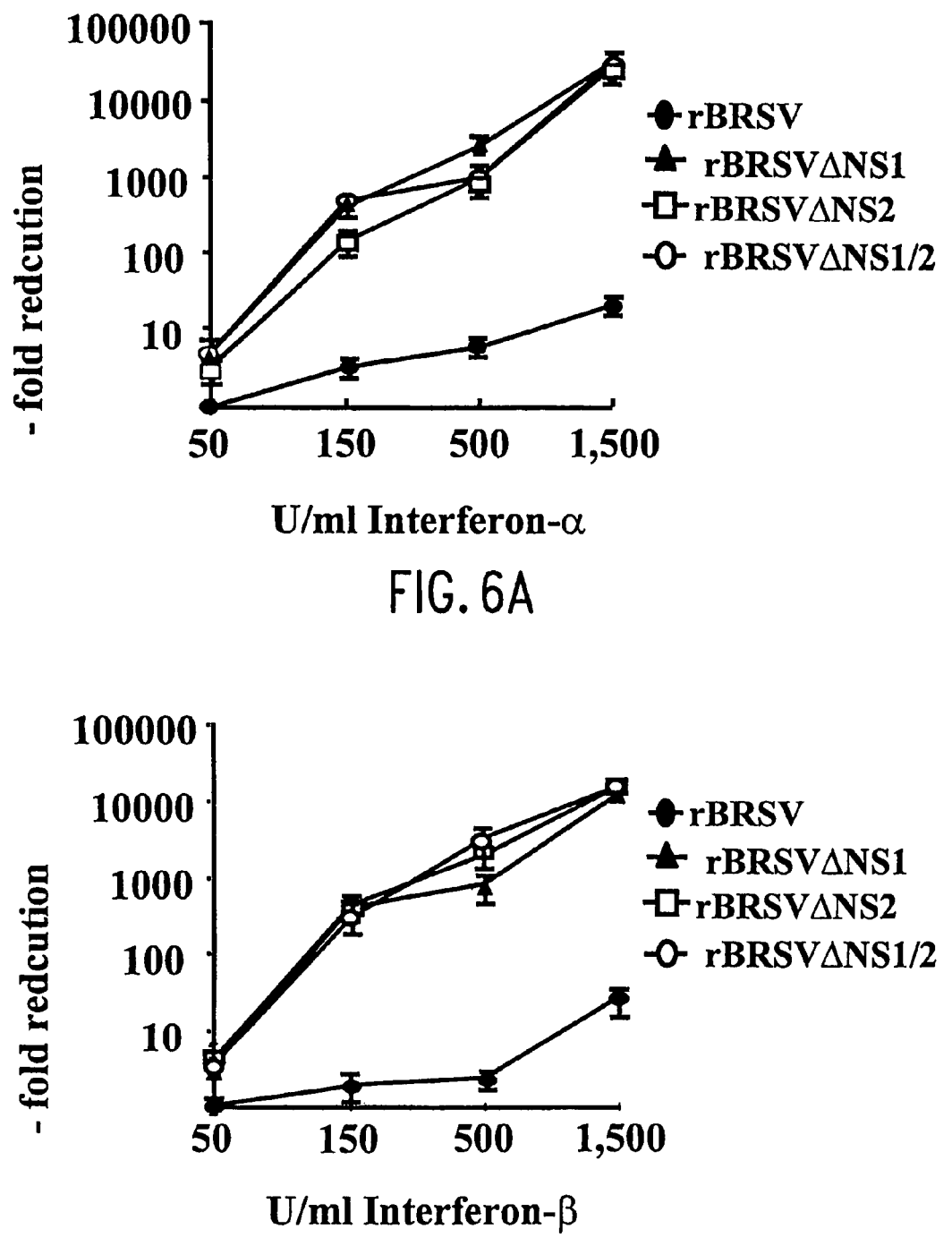

All three NS deletion mutants showed a very similar and dose-dependent susceptibility for the IFN induced cellular response wherein 1,500 U resulted in an about 10,000 fold reduction in infectious titers (FIG. 6). The wt BRSV on the other hand was relatively resistant to IFN treatment. The protection was not complete, however, and 1,500 U IFN alpha or IFN beta caused an about 13 fold reduction.

Figure 7:
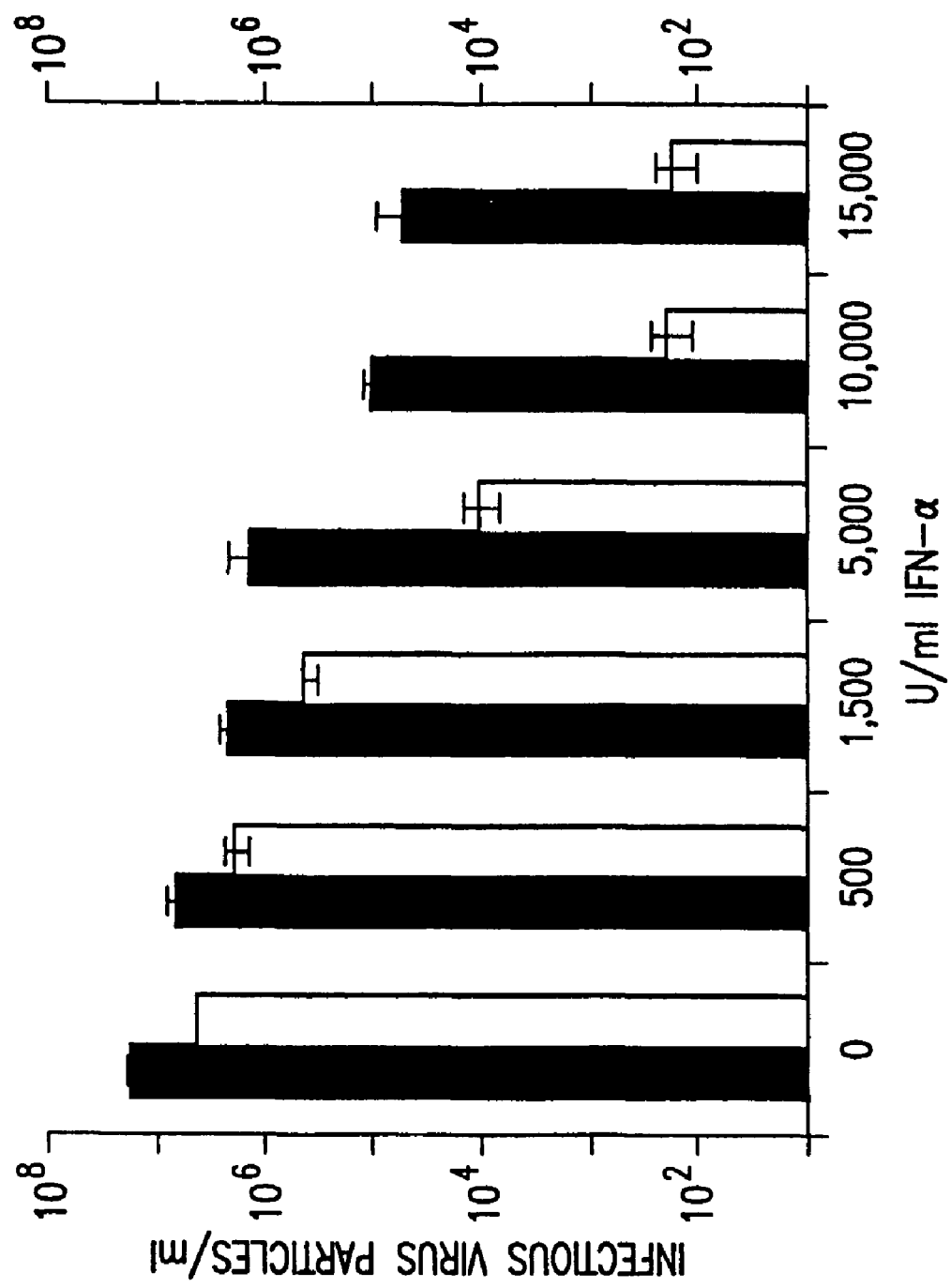
FIG. 7. The IFN resistance of BRSV is more pronounced in bovine cells than in primate cells. MDBK (filled columns) or Vero cells (open columns) were infected with rBRSV in a MOI of 1 and treated with recombinant IFN alpha A/D in the amounts indicated. Infectious virus titers were determined 3 days following infection.

To assess the possibility that the protection of wt BRSV in bovine cells is more pronounced than in the Vero primate cell line we infected MDBK and Vero cells in a MOI of 1 in parallel experiments and added the same amounts of IFN. In untreated MDBK and Vero cells BRSV grew to the same titers of $1.7 \times 10^7$ and $4 \times 10^6$ pfu/ml, respectively (FIG. 7). With IFN treatment the titers in Vero cells decreased faster than in MDBK cells. After addition of 10,000 U IFN the infectious titers in Vero cells were 555 times lower than in MDBK cells although the latter already showed considerable cellular damages. The strong inhibition of the NS deletion mutants demonstrated that the antiviral response of MDBK cells has at least the same strength as that of Vero cells. Therefore the enhanced protection of wt BRSV in MDBK cells suggests that BRSV deals more efficiently with the bovine cellular antiviral response than with that of primate cells.

Example 6

BRSV NS1 and NS2 Together Enhance the Resistance of Rabies Virus to the IFN Mediated Antiviral Response The deletion of each NS gene of BRSV resulted in about the same degree of sensitivity to IFN mediated cellular responses. This suggests that both NS proteins are required to counteract the antiviral mechanisms. To confirm the obligatory cooperative function of NS1 and NS2 and to find out whether the two NS proteins may be used for protection of a non-related virus, we developed recombinant rabies viruses expressing either NS1 (SAD VB-NS1) or NS2 (SAD VB-NS2). Recombinant RVs containing an additional NS1 or NS2 gene (FIG. 1) were constructed on the basis of full length RV cDNA (SAD L16) which comprises an additional transcriptional stop and restart sequence within the 3' non-coding sequence of the G gene (SAD VB) (32). The additional gene was introduced between the G and L genes of attenuated rabies virus SAD L16 (FIG. 1B), a method which has already been successful for other genes (12; 39). First cDNAs were constructed including versions of BRSV NS1 or NS2 proteins with C-terminal protein tag. Additional 27 nucleotides corresponding to an internal region of influenza hemagglutinin (HA) protein were introduced directly prior to the NS1 stop codon by means of PCR using the reverse primer NS1HAr-EcoRI (5'-GCAATAGAATTCCTAAGCGTAATCTGG-TACATCATAAGGATAATTCAGACCAAGA AGAGT-3') (SEQ ID NO:3) (containing an EcoRI restriction site; underlined). In the case of NS2, 24 nucleotides corresponding to the synthetic FLAG peptide were introduced using the reverse primer NS2FLr-EcoRI (5'-GCAATAGAATTCCTATT-TATCGTCATCATCTTTATAATCTGGATT-TAAATCATACT TATA-3') (SEQ ID NO:4) (EcoRI underlined). These PCR fragments were used to replace the corresponding sequences of a plasmid (pBSBRSVNS1NS2) containing nt 1 to nt 957 of the full length BRSV cDNA (5). The NS1-HA gene was excised with NotI and EcoRI. After a fill-in reaction with Klenow polymerase the 475 nt fragment was introduced in the unique SmaI site of pSAD VB immediately downstream of the additional transcriptional start signal. This gave pSAD VB-NS1HA. A 470 nt NS2-FL fragment was cloned in a similar manner after excision with AseI and EcoRI and filling in with Klenow polymerase resulting in pSAD VB-NS2FL.

Recombinant RV with either the NS1 or the NS2 gene was obtained as described previously (19) following transfection (CaPO$_4$ protocol; Mammalian Transfection Kit, Stratagene) of T7 promoter-controlled plasmids with the respective virus cDNA (10 µg). Plasmids encoding the RV proteins N (pTITB-N, 5 µg), P and L (PTITB-P and pTITB-L, 2.5 µg per plasmid) were co-transfected with the respective viral cDNAs into about $10^6$ BSR T7/5 cells stably expressing phage T7 RNA polymerase (5). After 4 hours, the transfection medium was removed and replaced by BHK-21 medium (Gibco) containing 10% FCS. Cell culture supernatants were harvested 6 days following transfection and added to new BSR cells. The detection of infectious RVs was performed by immune staining using an FITC conjugate (Centocor) recognizing the RV nucleoprotein N.

Recombinants could be obtained from cDNA in BSR T7/5 cells expressing the N, P, and L RV proteins from transfected plasmids. Expression of the NS proteins obviously had no adverse effect on replication, growth characteristics and infectious titers of the recombinants in BSR cells (not shown).

To examine the activity of the BRSV proteins expressed Vero cells were infected with parental RV (SAD VB) or individually with each of the recombinants or co-infected with the two recombinants SAD VB-NS1 and SAD VB-NS2. Infection with recombinants RV SAD VB, SAD VB-NS1 and SAD VB-NS2, respectively, was performed as described previously (18) in suspension using a MOI of 5. For co-infection with SAD VB-NS1 and SAD VB-NS2 a MOI of 2.5 was used for each recombinant. Recombinant universal type I interferon A/D was added up to concentrations of 500 U/ml directly after dilution of the cells. The virus titers were determined two days after infection by dilution series and immune staining with an FITC conjugate directed against the RV protein N (Centocor). In addition the expression of RV proteins was examined two days after infection in at least 4 independent experiments.

The growth of parental RV SAD VB and the viruses expressing NS1 or NS2 protein of the single infections was affected to the same extent (FIG. 8A). Upon addition of 50 IU IFN alpha the titers dropped by about 1 log and then decreased further very slowly with increasing amounts of IFN. This indicates a weak IFN response of Vero cells or a high intrinsic resistance of RV to the IFN mediated response in Vero cells. In cells co-transfected with viruses expressing NS1 and NS2, however, a protection of virus replication could be demonstrated. The virus titers remained significantly higher than in the single infections and decreased only slowly in a dose-dependent manner.

To assess again the above observation that the NS proteins of BRSV can block the antiviral response of bovine cells more efficiently than that of Vero cells experiments were conducted in parallel in MDBK cells (FIG. 8B). Standard RV SAD VB and the recombinants expressing NS replicated in untreated MDBK cells to slightly lower titers than in Vero cells. In contrast to Vero cells an IFN treatment reduced the infectious titers of the single infections of wt RV and the viruses expressing NS to a significant extent. An immediate decrease of the infectious titers by 3 log grades indicated a highly efficient IFN mediated cellular response. Despite this response, however, in cells co-infected with SAD VB-NS1 and SAD VB-NS2 the virus replication was completely protected up to amounts of 150 IU IFN added. These results could be confirmed by an analysis of RV protein synthesis. In untreated cells all recombinants produced similar amounts of RV proteins while in IFN treated cells only the co-infections were capable of performing significant protein synthesis until addition of more than 150-200 IU (not shown).

The results mentioned above show that both BRSV NS proteins are not only capable of conferring resistance to the IFN mediated antiviral response to BRSV but also to another non-related virus. In addition, the results confirm that both NS proteins are necessary and sufficient to exert the IFN antagonizing effect.

Example 7

Interferon Resistance of Clinical Isolates of Human RSV (HRSV)

In order to show that also HRSV has defense mechanisms against interferon experiments were carried out with clinical isolates of hospitalized patients. The isolates were obtained from a multicenter study coordinated by Prof. Werchau of Ruhr University at Bochum. Four isolates were obtained from patients treated in German hospitals due to diagnosed "bronchiolitis" (#61; #86; #109, and #110; group 1) and three isolates were obtained from patients with diagnosed "obstructive bronchitis" (#104; #112, and #162; group 2).

To prevent an adaptation of these clinical isolates to cell lines they were propagated on Hep2 cells for two passages and employed in the subsequent experiments. Growth curves of these isolates were determined with Hep2 cells. While isolates #61; #86; and #109 of group 1 in addition to isolate #112 of group 2 grew quickly in Hep2 cells and attained similarly high infectious titers between $3 \times 10^6$ and $4 \times 10^7$ pfu/ml after 3 days, isolates #110 of group 1 as well as #104 and #162 of group 2 were clearly attenuated in growth and attained only titers of only $3 \times 10^4$ pfu/ml after 3 days (FIG. 9). These differences in growth were also observed in primary respiratory epithelium cells: while #61; #86; #109 and #112 clearly induced the formation of syncytia, only single cell infections could be detected for isolates #110, #104 and #162 after the same infection period (not shown).

For determining the interferon resistance of the individual isolates Hep2 cells were infected with the different isolates (MOI=0.1) for 1 hour and then recombinant type I interferon A/D was applied in concentrations of 150 to 5,000 U/ml. After an incubation period of 72 hours, the virus titers of the individual clinical isolates were determined by means of end point titration. In this respect it was observed that all clinical HRSV isolates regardless of their growth rate were protected from the antiviral effect of recombinant type I IFN. Only with very high IFN concentrations of 5,000 U/ml the replication competence of the different clinical HRSV isolates was reduced by only 10 fold (FIG. 10). These data show that all clinical HRSV isolates are capable of counteracting the antiviral effect of high concentrations of recombinant type I IFN and this to at least the same extent as the HRSV laboratory strain Long (see FIG. 7).

The NS1 and NS2 genes of the isolates were amplified by RT-PCR and their sequences were determined. It was established that both genes are highly conserved confirming the results of the IFN assay. Both for the NS1 and the NS2 protein only very slight differences in the amino acid sequence occurred compared to the HRSV Long strain and among isolates. The NS2 protein of HRSV Long and the NS1 proteins of the clinical isolates #104, 112, 61, and 110 are identical. Each of the isolates #162, 86, and 109 contained one amino acid substitution with respect to the HRSV Long sequence (#86: N(76)S, #162: V(82)M, #109 E(91)G). The NS2 proteins of all clinical isolates are identical in their amino acid sequences and differ from HRSV Long by 2 substitutions DN(7,8)GT and T(21)1. Therefore the NS proteins and genes, respectively, of HRSV Long were used for further experiments.

Example 8

The NS1 And NS2 Proteins Of Human RSV (HRSV) Together Enhance the Resistance of Rabies Virus to the IFN Mediated Antiviral Response.

In order to demonstrate that both NS proteins of HRSV have an IFN type I antagonizing effect and that this function may be transferred to another non-related virus recombinant rabies viruses were developed expressing either NS1 (SAD VB-hNS1) or NS2 (SAD VB-hNS2) of HRSV (Long strain). Recombinant RVs with additional NS1 or NS2 gene (FIG. 11) were constructed on the basis of full length RV cDNA (SAD L16) containing an additional transcriptional stop and restart sequence in the 3' non-coding sequence of the G gene (SAD VB) (32). The additional gene was introduced between the G and L genes of attenuated rabies virus SAD L16 (FIG. 1B) as already described for the NS genes of BRSV. The cDNAs of the two HRSV genes were obtained by means of RT-PCR. For this purpose total RNA was isolated from HRSV (Long) infected Vero cells. For the NS1 gene the following primers were used: hNS1-Ncol5' (5'-ATT GAC CAT GGG CAG CAA TTC ATT-3'; first strand synthesis and PCR) (SEQ ID NO:5) and hNS1-EcoRI5' (5'-ATT GAG AAT TCT TAT GGA TTA AGA TCA AA-3') (SEQ ID NO:6), for the NS2 gene the primers hNS2-Ncol5' (5'-ATT GAC CAT GGA CAC AAC CCA CA-3') (SEQ ID NO:7) and hNS2-EcoRI3' (5'-ATT GAG AAT TCT TAT GGA TTG AGA TCA TA-3') (SEQ ID NO:8). After restriction with the NotI and EcoRI restriction enzymes these PCR fragments were clone into TIT plasmid cut in the same manner (pTIT-hNS1, pTIT-hNS2). Then, the NS1 gene was amplified from pTIT-hNS1 using PCR with the primers hNS1-Not5' (5'-TAT GAA GCG GCC GCC CCC TCT CTT CTT TCT ACA GAA AAT GGG CAG CAA TTC ATT GAG-3') (SEQ ID NO:9) and hNS1-EcoRI3' and digested with the NotI and EcoRI restriction enzymes. After a fill-in reaction with Klenow polymerase the fragment was introduced into the unique SmaI site of pSAD VB immediately downstream of the additional transcriptional start signal. This rendered pSAD VB-hNS1. The NS2 gene was amplified from pTIT-hNS2 using primer hNS2-AseI5' (5'-ATA CTT ATT AAT TGG GGC AAA TAA ATC AGT TCC CCA ACC AGC CAT GGA CAC AAC CCA CAA TG-3') (SEQ ID NO:10) and hNS2-Acc6513' (5'-ATA AAT GGT ACC AAA AGA TAA CAC TGT GTG AAT TAA ATT TTG AAA AGT GCT TAT GGA TTG AGA TCA TAC TTG-3') (SEQ ID NO:11), cut with AseI and EcoRI and after filling in with Klenow polymerase was cloned in a manner similar to the hNS1 gene. This resulted in pSAD VB-hNS2 (FIG. 11).

Recombinant RV containing either the NS1 or the NS2 gene of HRSV were obtained as described previously (19) following transfection (CaPO$_4$ protocol; Mammalian Transfection Kit, Stratagene) of T7 promoter-controlled plasmids using the respective virus cDNA (10 µg). Plasmids encoding the RV proteins N (pTITB-N, 5 µg), P and L (PTITB-P and pTITB-L, 2.5 µg per each plasmid) were co-transfected with the respective viral cDNAs into about 10$^6$ BSR T7/5 cells stably expressing phage T7 RNA polymerase (5). After 4 hours, the transfection medium was removed and replaced by BHK-21 medium (Gibco) containing 10% FCS. Cell culture supernatants were harvested 6 days following transfection and added to new BSR cells. The detection of infectious RVs was performed by immune staining using an FITC conjugate (Centocor) recognizing the RV nucleoprotein N. Expression of the HRSV NS proteins obviously had no adverse effect as to the replication, growth characteristics, and infectious titers of the recombinant RVs in BSR cells (not shown).

To examine the activity of the HRSV proteins expressed MDBK cells were infected with parental RV (SAD VB) or with each of the individual recombinants or co-infected with the two recombinants SAD VB-hNS1 and SAD VB-hNS2. Infection with the recombinants RV SAD VB, SAD VB-hNS1 and SAD VB-hNS2, respectively, was carried out as already described (18) in suspension using a MOI of 5. For co-infection with SAD VB-hNS1 and SAD VB-hNS2 a MOI of 2.5 was used for each recombinant. Recombinant universal type I interferon A/D was added directly after diluting the cells in concentrations of 50-500 U/ml. The virus titers were determined two days following infection by dilution series and immune staining with an FITC conjugate directed against the N RV protein (Centocor). The IFN treatment clearly reduced infectious titers of the single infections of wt RV and of the viruses expressing hNS. An addition of only 50 U IU IFN alpha resulted in a drop in infectious titers by 3 orders of magnitude. In cells co-infected with SAD VB-hNS1 and SAD VB-hNS2, however, the virus replication was clearly protected up to amounts of 150 IU IFN added (FIG. 11).

These results demonstrate that also the two HRSV NS proteins are able to antagonize the cellular response to IFN and to render a non-related virus resistant to the IFN mediated antiviral response. In addition, the results confirm that both NS proteins are necessary and sufficient to exert the IFN antagonizing activity.

Example 9

The NS1 and NS2 Proteins of Murine Pneumovirus (Pneumonia Virus of Mice; PVM) Together Enhance The Resistance Of Rabies Virus to The IFN Mediated Antiviral Response In order to demonstrate that also the two NS proteins of PVM mediate IFN type I resistance and that this function may be transferred to rabies virus, recombinant rabies viruses were developed expressing either NS1 (SAD VB-mNS1) or NS2 (SAD VB-mNS2) of PVM. The cDNAs of the two PVM genes were kindly provided by Andrew Easton; University of Warwick, U.K. (GenBank acc. No. D10331; FIG. 18). Recombinant RVs with an additional NS1 or NS2 gene (FIG. 11) were also constructed on the basis of SAD VB (32; see Examples 6 and 8). The additional gene was introduced between the G and L genes of RV SAD L16 (FIG. 1B) as already described above for the NS genes of BRSV. The genes of the two NS proteins were amplified by means of PCR introducing into the NS1 gene 27 additional nucleotides encoding an internal region of influenza hemagglutinin (HA) protein (HA tag) immediately prior to the translational stop codon. Immediately upstream of the stop codon of the NS2 gene 24 nucleotides were introduced encoding a synthetic FLAG peptide (FLAG tag). For the NS1 gene of PVM the following primers were used: mNS1-NotlEcoRV5' (5'-AAT GAT ATC GCG GCC GCC CCC TCT CTT CTT TCT ACA GAA ATG GGC TGT AAT GTG ATG ATG-3') (SEQ ID NO:12) and mNS1ha-EcoRI/V3' (5'-AAT GAT ATC GAA TTC TTA AGC GTA ATC GG TAC ATC ATA AGG ATA ACC ACT GAT CAG CTC TAC-3') (SEQ ID NO:13), for the NS2 gene of PVM the primers mNS2-AseIEcoRV5' (5'-AAT GAT ATC ATT AAT TGG GGC AAA TAA ATC AGT TCC CCA ACC AGC CAT GTC CAC AGC TAT GAA CAA G-3') (SEQ ID NO:14) and mNS2fl-EcoRI/V3' (5'-AAT GAT ATC GAA TTC TCA TTT ATC GTC ATC ATC TTT ATA GTC ATC ATC ATC CTC ATC-3') (SEQ ID NO:15). After digestion with the restriction enzyme EcoRV these PCR fragments were then introduced into the unique SmaI site of pSAD VB immediately downstream of the additional transcriptional start signal. This gave pSAD VB-mNS1 and pSAD VB-mNS2 (FIG. 11).

Recombinant RV containing either the NS1 or the NS2 gene of PVM were obtained in BSR T7/5 cells expressing the RV proteins N, P, and L from transfected plasmids as already described in Examples 6 and 8. The expression of the NS proteins obviously had no adverse effect as to the replication, growth characteristics, and infectious titers of the recombinants in BSR cells (not shown).

To assess the activity of the PVM proteins expressed MDBK cells were infected with parental RV (SAD VB) or with each of the individual recombinants or co-infected with the two recombinants SAD VB-mNS1 and SAD VB-mNS2. Infection with the recombinants RV SAD VB, SAD VB-mNS1 and SAD VB-mNS2, respectively, was carried out as already described (18) in suspension using a MOI of 5. For co-infection with SAD VB-mNS1 and SAD VB-mNS2 a MOI of 2.5 was used for each recombinant. Recombinant universal type I interferon A/D was added directly after diluting the cells in concentrations of 50-500 U/ml. The virus titers were determined two days following infection by dilution series and immune staining using an FITC conjugate directed against the N RV protein (Centocor). The IFN treatment clearly reduced infectious titers of the single infections of wt RV and of the viruses expressing hNS. In cells co-infected with SAD VB-mNS1 and SAD VB-mNS2, however, the virus replication was clearly protected up to amounts of 100 IU IFN added (FIG. 13).

These results demonstrate that also the two PVM NS proteins are able to antagonize the cellular response to IFN and to render a non-related virus resistant to the IFN mediated antiviral response. Since the homology of the PVM NS proteins to those of HRSV is only 17% (for NS1) and 20% (for NS2) the INF antagonizing function was unpredictable. As already observed for the NS proteins of BRSV and HRSV also in the case of PVM both NS proteins are necessary and sufficient to exert the IFN antagonizing activity.

Example 10

Preparation of Recombinant BRSV Harbouring Heterologous NS Genes

We further constructed recombinant chimeric BRSVs by replacing the own BRSV genes by NS genes from other pneumoviruses.

For the preparation of recombinant BRSVs containing the NS1 gene of HRSV or PVM instead of the BRSV NS1 gene a plasmid was used containing nt 1 through 957 of the full length BRSV cDNA (5) and which in addition has an EcoRI restriction site in the NS1 gene at nt 311 (pbNS1EcoRIbNS2). In this manner the complete coding region of the NS2 gene may be removed by digestion with NotI and EcoRI restriction enzymes. The HRSV and the PVM NS1 gene were amplified by means of PCR using primers hNS1-NotI5' and hNS1-EcoRI3' for HRSV NS1 and mNS1-NotIEcoRV5' and mNS1ha-EcoRI3' for PVM NS1, and after digestion with NotI and EcoRI restriction enzymes were introduced in a plamsid giving phNS1bNS2 and pmNS1bNS2. Afterwards, both plasmids were digested with NotI and AccI and the resulting fragments of 1094 nt length for hNS1bNS2 and 1043 nt length for mNS1bNS2, respectively, were inserted into the full length BRSV cDNA. This rendered rBRSV hNS1bNS2 and rBRSV mNS1bNS2 FIG. 14).

For the preparation of BRSVs carrying heterologous NS2 genes (rBRSV bNS1hNS2 and rBRSV bNS1mNS2), pNS1NS2 (5) was first cut with restriction enzyme Acc651 and then partially with restriction enzyme AseI excising a 446 nt fragment comprising the NS2 gene. Into this site a fragment was then introduced containing the hNS2 or the mNS2 gene, respectively. These fragments were generated by PCR using primers hNS2-AseI5' and hNS2-Acc6513' for the HRSV NS2 gene or mNS2-AseIEcoRV5' and mNS2-Acc6513' (5'-ATA AAT GGT ACC AAA AGA TAA CAC TGT GTG AAT TAA ATT TTG AAA AGT GCT CAT TTA TCG TCA TCA TCT TTA TAG-3') (SEQ ID NO:16) for the PVM NS2 gene. The fragments were subsequently digested with restriction enzymes AseI and Acc651 and introduced into pNS1 NS2 giving pbNS1 hNS2 and pbNS1 mNS2. These plasmids were then digested with restriction enzymes NotI and Acc651 and the resulting fragments (949 nt for bNS1 hNS2 and 1069 nt for bNS1 mNS2) were inserted in the full length BRSV cDNA rendering rBRSV bNS1hNS$_2$ and rBRSV bNS1mNS2 (FIG. 14).

For the preparation of recombinant BRSVs containing both NS genes of HRSV and PVM, respectively, plasmids phNS1bNS2 and pmNS1bNS2 were first cut with restriction enzyme Acc651 and then partially with restriction enzyme AseI. Afterwards, the fragments described above of the HRSV NS2 gene and the PVM NS2 gene were introduced into the respective plasmids giving phNS1hNS2 and pmNS1mNS2. Also these plasmids were digested with restriction enzymes NotI and Acc651 and the resulting fragments of 1094 nt for hNS1hNS2 and 1163 nt for mNS1mNS2 were inserted into full length cDNA of BRSV. This gave rBRSV hNS1hNS2 and rBRSV mNS1mNS2 (FIG. 14).

Viable recombinant viruses rBRSV hNS1bNS2, rBRSV bNS1hNS2 and rBRSV hNS1hNS2 as well as rBRSV mNS1bNS2, rBRSV bNS1mNS2 and rBRSV mNS1mNS2 could be obtained from the respective cDNA constructs in BSR T7/5 cells (5) following transfection (CaPO$_4$ protocol; Mammalian Transfection Kit, Stratagene) of T7 promoter-controlled plasmids using the respective virus cDNAs (10 µg). Plasmids encoding the BRSV proteins N and P (PTITB-N and pTITB-P, 4 µg per each plasmid) and L and M2 (PTITB-L and pTITB-M2, 2 µg per each plasmid) were co-transfected with each virus cDNA into about 10$^6$ BSR T7/5 cells stably expressing RNA polymerase of phage T7 (5). After 4 hours, the transfection medium was removed and BHK-21 medium (Gibco) containing 5% FCS was added. Cells transfected with BRSV cDNA were diluted in a ratio of 1:3 every 5 days until a cytopathogenic effect could be observed.

In all cases co-transfection of the support plasmids encoding the N, P, L, and M2 proteins of BRSV resulted in the formation of syncytia. After dilution of the cells in a ratio of 1:3 and occurrence of a clear cytopathogenic effect the viruses were harvested.

For the preparation of virus stock solutions 80% confluent Vero cells were infected with a multiplicity of infection (MOI) of 0.1 in Dulbecco's minimal essential medium (DMEM) without serum. After adsorption for one hour the inoculum was removed and the cells were incubated at 37° C. in DMEM supplemented with 2.5% FCS in a 5% CO$_2$ atmosphere until a clear cytopathic effect (CPE) was observed after approx. 4 days. The viruses were released by freezing and subsequent thawing. The virus titers on Vero cells were determined by dilution series in microtiter plates followed by counting of infected foci. For this purpose the foci were stained by indirect staining using an antibody against the F fusion protein (SEROTEK, U.K.).

Example 11

Growth of the BRSV Chimeras: The IFN Resistance is Cell Type Dependent

The growth characteristics of the viruses were first analyzed in Vero cells. While BRSV hNS1hNS2 and BRSV hNS1bNS2 behaved similar to BRSV wt, BRSV mNS1mNS2 and BRSV mNS1bNS2 were slightly attenuated as compared to the parental full length virus. This indicates that the function(s) of the BRSV NS proteins in virus replication are performed by the HRSV NS protein to the full extent. Both the parental wt BRSV and the two HRSV/BRSV chimeras attained infectious titers of about 5×10$^5$ pfu following infection of Vero cells with a MOI of 0.1 and a subsequent incubation period of 3 days (FIG. 15). The PVM/BRSV chimeras on the other hand achieved only about 4×10$^5$ pfu after 3 days indicating that the PVM NS genes are not optimal to perform the function of the BRSV (and HRSV) genes in virus replication.

Subsequently, a cell line of bovine origin, MDBK, was used which is optimal in supporting the growth of wt BRSV and in contrast to Vero cells has a functional IFN type I system (5). In this case the growth of BRSVhNS1hNS2 was reduced compared to wt BRSV. A titer of only 4×10$^4$ pfu was achieved after 3 days in contrast to BRSV which grows up to 1×10$^6$ pfu (FIG. 16). In the optimal host cell for wt BRSV, bovine MDBK cells, the growth of BRSV hNS1hNS2 obviously is attenuated while no attenuation can be observed in the IFN-negative Vero cells.

Recombinant human type I interferons were then used to analyze the behavior of wt BRSV and BRSV hNS1hNS2 in IFN stimulated cells. To study the effect of type I interferon on the replication of recombinant Vero or MDBK cells were infected with the different viruses in a MOI of 0.1 as described above and seeded in six well dishes in DMEM containing 2.5% FCS. Recombinant universal type I interferon (human interferon alpha A/D, PBL Biomedical Laboratories) was added directly after seeding in concentrations of 500-10,000 U/ml. The virus titers were determined after an incubation period of three days by dilution series and indirect staining of infected cells with an antibody against the F fusion protein.

Figure 17B:
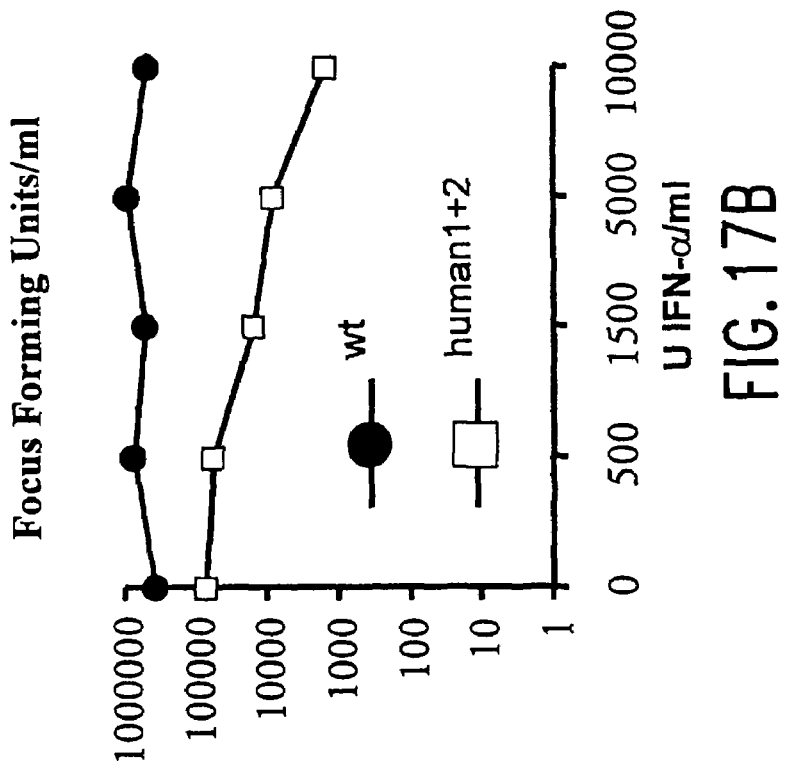
Figure 17A:
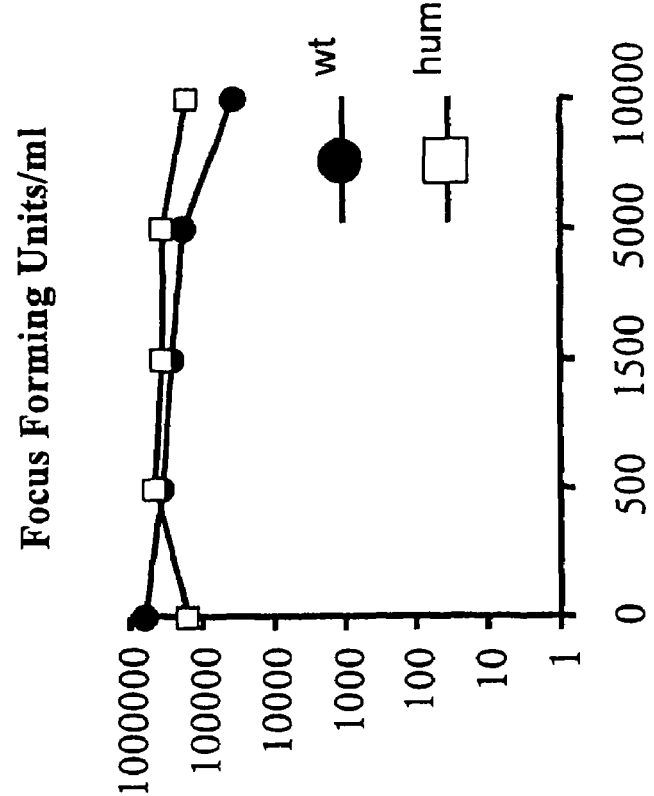

No difference could be observed on Vero cells between wt BRSV and BRSV hNS1hNS2 with respect to their IFN resistance. For both viruses a slight reduction of infectious titers could be observed only upon addition of 5000 U and more (FIG. 17A). In contrast on MDBK cells BRSV hNS1hNS2 showed a strong dose-dependent sensitivity to the IFN induced cellular response wherein as low as 1500 U resulted in a 3fold and 10,000 U in an about 30fold reduction in infectious titers. The wt BRSV on the other hand exhibited a high resistance to IFN treatment. Even 10,000 U IFN alpha did not affect the replication of wt BRSV (FIG. 17B). Although chimeric BRSV hNS1hNS2 shows an IFN resistance similar to that of wt BRSV in Vero cells it is unable to completely prevent the IFN induced antiviral response in cells of bovine origin. This demonstrates that the BRSV NS proteins are more successful in managing the bovine cellular antiviral response that the HRSV NS proteins. Obviously, the IFN antagonizing effect of NS proteins is suboptimal in heterologous host cells. Chimeric RS viruses carrying heterologous NS proteins are attenuated in vivo and may be used as live vaccines.

REFERENCES

1. Ahmadian, G., P. Chambers und A. J. Easton. 1999. Detection and characterization of proteins encoded by the second ORF of the M2 gene of pneumoviruses. J Gen Virol 80 (Pt 8):2011-2016.
2. Atreya, P. L. und S. Kulkarni. 1999. Respiratory syncytial virus strain A2 is resistant to the antiviral effects of type I interferons and human MxA. Virology 261:227-241.
3. Atreya, P. L., M. E. Peeples und P. L. Collins. 1998. The NS1 protein of human respiratory syncytial virus is a potent inhibitor of minigenome transcription and RNA replication. J Virol. 72:1452-1461.
4. Benningham, A., aud P. L. Collins. 1999. The M2-2 protein of human respiratory syncytial virus is a regulatory factor involved in the balance between RNA replication and transcription. Proc Natl Acad Sci USA 96:1 1259-11264.
5. Buchholz, U. J., S. Finke und K. K. Conzelmann. 1999. Generation of bovine respiratory syncytial virus (BRSV) from cDNA: BRSV NS2 is not essential for virus replication in tissue culture, and the human RSV leader region acts as a functional BRSV genome promoter. J Virol 73:251-259.
6. Buchholz, U. J., H. Granzow, K. Schuldt, S. S. Whitehead, B. R. Murphy und P. L. Collins. 2000. Chimeric bovine respiratory syncytial virus with glycoprotein gene substitutions from human respiratory syncytial virus (HRSV): Effects on host range and evaluation as a live-attenuated HRSV vaccine. J. Virol. 74:1187-1199.
7. Chaplin, P. J., K. R. Parsons und R. A. Collins. 1996. The cloning of cattle interferon-A subtypes isolated from the gut epithelium of rotavirus-infected calves. Immunogenetics 44:143-145.
8. Collins, P. L., M. G. Hill, E. Camargo, H. Grosfeld, R. M. Chanock und B. R. Murphy. 1995. Production of infectious human respiratory syncytial virus from cloned cDNA confirms an essential role for the transcription elongation factor from the 5' proximal open reading frame of the M2 mRNA in gene expression and provides a capability for vaccine development. Proc. Natl. Acad. Sci. U.S.A. 92:11563-11567.
9. Collins, P. L., K. Mcintosh und R. M. Chanock. 1996. Respiratory syncytial virus, S. 1313-1352— In B. N. Fields, D. M. Knipe, P. M. Howley, R. M. Chanock, J. L. Elnik, T. P. Onath, B. Oizman, and S. E. Traus (Hrsg.), Fields virology. Lippincott-Raven. Philadelphia, Pa.
10. Collins, P. L., und G. W. Wertz. 1985. Nucleotide sequences of the IB and 1C nonstructural protein mRNAs of human respiratory syncytial virus. Virology 143:442-451.
11. Conzelmann, K. K. 1998. Nonsegmented negative-strand RNA viruses: Genetics and manipulation of viral genomes. Annu. Rev. Genet. 32:123-162.
12. Conzelmann, K. K., J. H. Cox, L. G. Schneider und H. J. Thiel. 1990. Molecular cloning and complete nucleotide sequence of the attenuated rabies virus SAD B19. Virology 175:485-499.
13. Didcock, L., D. F. Young, S. Goodbourn und R. E. Randall. 1999a. Sendai virus and simian on antitermination protein of respiratory syncytial virus in sequential transcription. J. Virol 73:5852-5864.
14. Finke, S., und K. K. Conzelmann. 1997. Antisense gene expression from recombinant rabies virus: random packaging of positive- and negative-strand ribonucleoprotein complexes into rabies virions. J. Virol. 71 :7281-7288.
15. Finke, S., und K. K. Conzelmann. 1999. Virus promoters determine interference by defective RNAs: selective amplification of mini-RNA vectors and rescue from cDNA by a 3' copy-back antisense rabies virus. J. Virol 73:3818-3825.
16. Gale, M. J., C. M. Blakely, B. Kwieciszewski, S. L. Tan, M. Dossett, N. M. Tang, M. J. Korth, S. J. Polyak, D. R. Gretch und M. G. Katze. 1998. Control of PKR protein kinase by hepatitis C virus nonstructural 5A protein: molecular mechanisms of kinase regulation. Mol Cell Biol 18:5208-5218.
17. Gale, M. J. J., M. J. Korth, N. M. Tang, S. L. Tan, D. A. Hopkins, T. E. Dever, S. J. Polyak, D. R. Gretch und M. G. Katze. 1997. Evidence that hepatitis C virus resistance to interferon is mediated through repression of the PKR protein kinase by the nonstructural 5A protein. Virology 230: 217-227.
18. Garcin, D., P. Latorre und D. Kolakofsky. 1999. Sendai virus C proteins counteract the interferon-mediated induction of an antiviral state. J Virol 73:6559-6565.
19. Garcia-Sastre, A., R. K. Durbin, H. Zheng, P. Palese, R. Gertner, D. E. Levy und J. E. Durbin. 1998. The role of interferon in influenza virus tissue tropism. J Virol 72;8550-8558.
20. Garcia-Sastre, A., A. Egorov, D. Matassov, S. Brandt, D. E. Levy, J. E. Durbin, P. Palese und T. Muster. 1998. Influenza A virus lacking the NS1 gene replicates in interferon-deficient systems. Virology 252:324-330.
21. Grosfeld, H. M. G. Hill und P. L. Collins. 1995. RNA replication by respiratory syncytial virus (RSV) is directed by the N, P, and L proteins; transcription also occurs under these conditions but requires RSV superinfection for efficient synthesis of full-length mRNA. J. Virol. 69:5677-5686.
22. Hanada. N., T. Morishima, K. Nishikawa, S. Isomura und Y. Nagai. 1986. Interferon-mediated self-limiting growth of respiratory syncytial virus in mouse embryo cells. J Med Virol 20:363-370.
23. Hardy. R. W und G. W. Wertz. 1998. The product of the respiratory syncytial virus M2 gene ORF1 enhances readthrough of intergenic junctions during viral transcription. J Virol 72:520-526.
24. Jin, H., X. Cheng, H-Z. Zhou, S. Li und R. Seid. 2000. Respiratory syncytial virus that lacks open reading frame 2 of the M2 gene (M2-2) has altered growth characteristics and is attenuated in rodents. J. Virol. 74;74-82.
25. Jin, H., D. Clarke, H. Z. Zhou, X. Cheng, K. Coelingh, M. Bryant und S. Li. 1998. Recombinant human respiratory syncytial virus (RSV) from cDNA an construction of subgroup A and B chimeric RSV. Virology 251:206-214.
26. Lerch, R. A., E. J. Stott und G. W. Wertz. 1989. Characterization of bovine respiratory syncytial virus proteins and mRNAs and generation of cDNA clones to the viral mRNAs. J Virol 63:833-840.
27. Mallipeddi, S. K., S. K. Samal und S. B. Mohanty. 1990. Analysis of polypeptides synthesized in bovine respiratory syncytial virus-infected cells. Arch Virol 115:23-36.
28. Mebatsion, T., M. J. Schnell. J. H. Cox. S. Finke. and K. K. Conzelmann. 1996. Highly stable expression of a foreign gene from rabies virus vectors. Proc. Natl. Acad. Sci. U.S.A. 93:7310-7314.
29. Mohanty, S. B., A. L. Ingling und M. G. Lillie. 1975. Experimentally induced respiratory syncytial viral infection in calves— Am J Vet Res 36;417-419.
30. Pastey, M. K., und S. K. Samal. 1995. Nucleotide sequence analysis of the nonstructural NS1 (1C) and NS2 (1B) protein genes of bovine respiratory syncytial virus. J. Gen. Virol. 76:193-197.
31. Ploegh, H. L. 1998. Viral strategies of immune evasion. Science 280:248-253.
32. Pringle, C. R. 1996. Virus taxonomy 1996~a bulletin from the Xth International. Congress of Virology in Jerusalem. Arch Virol 141; 2251-2256.
33. Pringle, C. R. 1998. The universal system of virus taxonomy of the International Committee on Virus Taxonomy (ICTV), including new proposals ratified since publication of the Sixth ICTV Report in 1995[news] [published erratum appears in Arch Virol 1998; 143(3):630]. Arch Virol 143;203-210.
34. Samal, S. K., M. K. Pastey, T. H. McPhillips und S. B. Mohanty. 1993. Bovine respiratory syncytial virus nucleocapsid protein expressed in insect cells specifically interacts with the phosphoprotein and the M2 protein. Virology 193:470-473.
36. Schnell. M. J., T. Mebatsion und K. K. Conzelmann. 1994. Infectious rabies viruses from cloned cDNA. EMBO J. 13:4195-4203.
37. Stott, E. J., L. H. Thomas, G. Taylor, A. P. Collins, J. Jebbett und S. Crouch. 1984. A comparison of three vaccines against respiratory syncytial virus in calves. J Hyg (Lond) 93:251-261.
38. Tan, S. L., und M. G. Katze. 1998. Biochemical and genetic evidence for complex formation between the influenza A virus NS1 protein and the interferon-induced PKR protein kinase. J Interferon Cytokine Res 18:757-766.
39. Taylor, D. R., S. T. Shi, P. R. Romano, G. N. Barber und M. M. Lai. 1999. Inhibition of the interferon-inducible protein kinase PKR by HCV E2 protein [see comments]. Science 285:107-110.
40. Teng, M. N., und P. L. Collins. 1999. Altered growth characteristics of recombinant respiratory syncytial viruses which do not produce NS2 protein. J Virol 73;466-473.
41. Uzé, G., G. Lutfalla und K. E. Mogensen. 1995. Alpha and beta interferons and their receptor and their friends and relations. J Interferon Cytokine Res 15:3-26.
42. van der Poel, W. H., A. Brand, J. A. Kramps und J. T. van Oirschot. 1994. Respiratory syncytial virus infections in human beings and in cattle. J Infect 29:215.228.
43. Wathelet, M. G., P. M. Berr und G. A. Huez. 1992. Regulation of gene expression by cytokines and virus in human cells lacking the type-I interferon locus. Eur J Biochem 206:901.910.
44. Weber, E., B. Humbert, H. J. Streckert und H. Werchau. 1995. Nonstructural protein 2 (NS2) of respiratory syncytial virus (RSV) detected by an antipeptide serum. Respiration 62:27-33.
45. Whitehead. S. S., A. Bukreyev. M. N. Teng. C. Y. Firestone, M. St Claire. W. R. Elkins. P. L. Collins und B. R. Murphy. 1999. Recombinant respiratory syncytial virus bearing a deletion of either the NS2 or SH gene is attenuated in chimpanzees. J Virol 73:3438-3442.
46. Yu, Q., R. W. Hardy und G. W. Wertz. 1995. Functional cDNA clones of the human respiratory syncytial (RS) virus N, P, and L proteins support replication of RS virus genomic RNA analogs and define minimal trans-acting requirements for RNA replication. J Virol 69:2412-2419.

The invention claimed is:

1. A method for reducing an Interferon (IFN) mediated immune response in an animal in need thereof, the method comprising administering to the animal a composition comprising a non RSV-related recombinant virus containing a polynucleotide encoding pneumovirus NS1 and/or NS2; wherein expression of the NS1 and/or NS2 reduces the IFN mediated immune response.

2. The method according to claim 1 wherein the immune response is an antiviral response.

3. The method according to claim 1 wherein the-polynucleotide encoding pneumovirus NS1 is used together with the polynucleotide encoding pneumovirus NS2.

4. The method according to claim 1 wherein the polynucleotides encoding NS1 and NS2 are derived from different pneumoviruses 5. The method according to claim 1 wherein the virus is adenovirus (AdV), adenoassociated virus (AAV), herpes virus, or pox virus.

6. The method according to claim 1 wherein the virus is from a Alpha-, Flavi- or Picornaviridae family.

7. The method according to claim 1 wherein the virus is derived from a segmented or non-segmented negative strand RNA virus.

8. The method according to claim 7 wherein the virus is from the families of Paramyxoviridae, Filoviridae, Bornaviridae, or Rhabdoviridae.

9. The method according to claim 1 wherein the composition further contains a vaccine.

10. The method according to claim 1 wherein the polynucleotide encoding NS1 and/or NS2 is derived from pneumovirus of mice (PVM).

11. The method according to claim 1 wherein IFN is type I interferon (IFN alpha or IFN beta).

12. The method of claim 1, wherein the expression of the pneumovirus NS1 and/or NS2 protein imparts to said virus or enhances the capability to escape and IFN mediated immune response.

13. The method according to claim 12 wherein the virus is rabies virus.

14. The method according to claim 1 wherein the polynucleotide encoding pneumovirus NS1 and/or NS2 is derived from BRSV, HRSV, or PVM.

15. The method according to claim 14 wherein the polynucleotide encodes a protein-having an amino acid sequence selected from the group consisting of SEQ ID NOs 17, 18, 19, 20, 21 or 22.

* * * * *